(12) United States Patent
Ohrui et al.

(10) Patent No.: US 8,952,873 B2
(45) Date of Patent: Feb. 10, 2015

(54) FUSED POLYCYCLIC COMPOUND AND ORGANIC LIGHT-EMITTING DEVICE USING THE COMPOUND

(75) Inventors: Hiroki Ohrui, Kawasaki (JP); Hironobu Iwawaki, Yokohama (JP); Kei Tagami, Yokohama (JP); Masanori Muratsubaki, Hachioji (JP); Ryuji Ishii, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 455 days.

(21) Appl. No.: 13/461,276

(22) Filed: May 1, 2012

(65) Prior Publication Data

US 2012/0306727 A1 Dec. 6, 2012

(30) Foreign Application Priority Data

May 30, 2011 (JP) ................. 2011-120164

(51) Int. Cl.
| | |
|---|---|
| C07C 255/50 | (2006.01) |
| C07D 235/18 | (2006.01) |
| C07D 498/04 | (2006.01) |
| C09K 11/06 | (2006.01) |
| H05B 33/14 | (2006.01) |
| C07C 255/51 | (2006.01) |
| H01L 51/00 | (2006.01) |
| H01L 51/50 | (2006.01) |

(52) U.S. Cl.
CPC ............ *C07C 255/50* (2013.01); *C07C 255/51* (2013.01); *C07D 235/18* (2013.01); *C07D 498/04* (2013.01); *C09K 11/06* (2013.01); *H01L 51/0056* (2013.01); *H05B 33/14* (2013.01); *C07C 2103/54* (2013.01); *H01L 51/0054* (2013.01); *H01L 51/0058* (2013.01); *H01L 51/0061* (2013.01); *H01L 51/0072* (2013.01); *H01L 51/5012* (2013.01); *C09K 2211/1011* (2013.01); *C09K 2211/1029* (2013.01); *C09K 2211/1033* (2013.01); *C09K 2211/1044* (2013.01)
USPC .......... 345/76; 313/504; 546/115; 548/305.1; 558/411; 585/26

(58) Field of Classification Search
None
See application file for complete search history.

(56) References Cited

U.S. PATENT DOCUMENTS

| | | | |
|---|---|---|---|
| 7,794,855 B2 | 9/2010 | Iwawaki et al. | |
| 7,919,197 B2 | 4/2011 | Negishi et al. | |
| 7,919,198 B2 | 4/2011 | Negishi et al. | |
| 7,977,869 B2 | 7/2011 | Saitoh et al. | |
| 7,981,525 B2 | 7/2011 | Hashimoto et al. | |
| 7,998,597 B2 | 8/2011 | Saitoh et al. | |
| 8,021,766 B2 | 9/2011 | Muratsubaki et al. | |
| 8,026,664 B2 | 9/2011 | Saitoh et al. | |
| 8,034,944 B2 | 10/2011 | Ohrui et al. | |
| 8,072,137 B2 | 12/2011 | Ohrui et al. | |
| 8,293,384 B2 | 10/2012 | Kamatani et al. | |
| 8,507,900 B2 | 8/2013 | Mizuki | |
| 8,790,795 B2 * | 7/2014 | Iwawaki et al. ............ | 428/690 |
| 2009/0015144 A1 | 1/2009 | Takashima et al. | |
| 2010/0127618 A1 | 5/2010 | Ohrui et al. | |
| 2010/0270914 A1 | 10/2010 | Kamatani et al. | |
| 2010/0327274 A1 | 12/2010 | Okajima et al. | |
| 2011/0140595 A1 | 6/2011 | Negishi et al. | |
| 2011/0147731 A1 | 6/2011 | Negishi et al. | |
| 2011/0147732 A1 | 6/2011 | Mizuki | |
| 2012/0025183 A1 | 2/2012 | Kamatani et al. | |
| 2014/0018539 A1 | 1/2014 | Mizuki | |

FOREIGN PATENT DOCUMENTS

| | | |
|---|---|---|
| CN | 101870705 A | 10/2010 |
| EP | 2085371 A1 | 8/2009 |
| EP | 2243761 A1 | 10/2010 |
| EP | 2314558 A1 | 4/2011 |
| JP | 2010-254610 A | 11/2010 |
| JP | 2010-270103 A | 12/2010 |
| WO | 2010018842 A1 | 2/2010 |
| WO | 2010123153 A1 | 10/2010 |

OTHER PUBLICATIONS

Chinese Office Action issued in counterpart application No. 201210165768.5 dated Dec. 23, 2013, along with its English-language translation—15 pages.
European Communication issued in counterpart application No. 12168005.2 dated Oct. 2, 2012—8 pages.
U.S. Appl. No. 13/480,608, filed May 25, 2012, with first-named inventor Hironobu Iwawaki.

\* cited by examiner

*Primary Examiner* — Kamal Saeed
(74) *Attorney, Agent, or Firm* — Fitzpatrick, Cella, Harper & Scinto

(57) ABSTRACT

Provided are a fused polycyclic compound suitable for use mainly as a component for a blue-light-emitting device, and an organic light-emitting device using the compound. The fused polycyclic compound is represented by the general formulae (1), (2), (8) and (9).

9 Claims, 1 Drawing Sheet

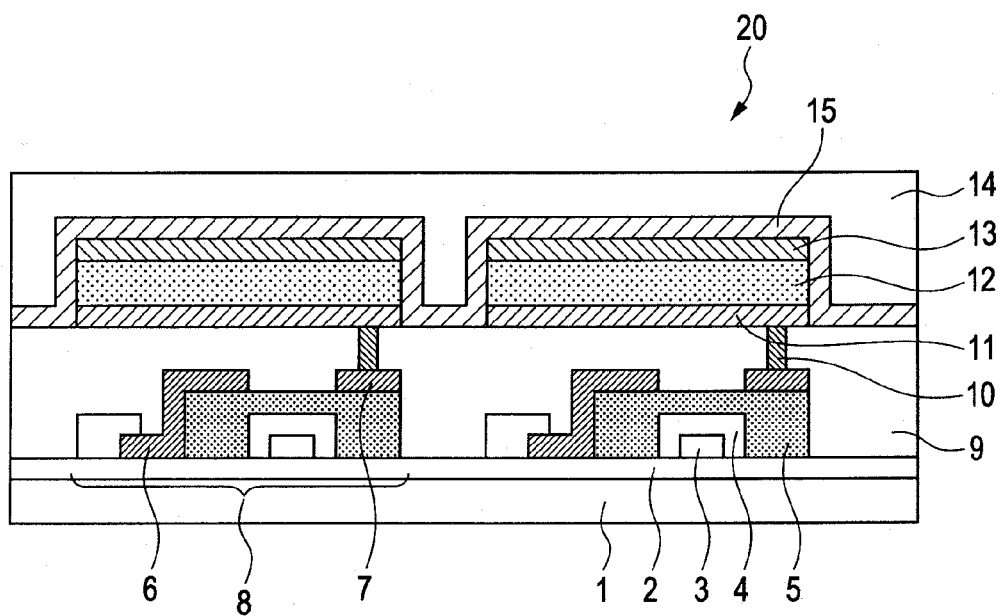

FUSED POLYCYCLIC COMPOUND AND ORGANIC LIGHT-EMITTING DEVICE USING THE COMPOUND

BACKGROUND OF THE INVENTION

1. Field of the Invention

The present invention relates to a fused polycyclic compound and an organic light-emitting device using the compound.

2. Description of the Related Art

An organic light-emitting device is an electronic element in which a thin film containing a fluorescent or phosphorescent organic compound is interposed between a pair of electrodes. When an electron and a hole are injected from the respective electrodes, an exciton of the fluorescent or phosphorescent compound is produced, and the organic light-emitting device emits light upon return of the exciton to its ground state.

Recent advances in the organic light-emitting device are remarkable, and have resulted in the following features, for example. That is, the organic light-emitting device emits light having high luminance at a low applied voltage and a variety of emission wavelengths, has high-speed responsiveness, and allows a light-emitting device to be reduced in thickness and weight. This suggests that the organic light-emitting device can be used for a wide range of applications.

By the way, research has been vigorously conducted on fluorescent or phosphorescent organic compounds to be used as components for organic light-emitting devices. An organic compound described in, for example, Japanese Patent Application Laid-Open No. 2010-254610 or Japanese Patent Application Laid-Open No. 2010-270103 has been proposed as a blue-light-emitting material out of the compounds.

However, the organic compound proposed in Japanese Patent Application Laid-Open No. 2010-254610 or Japanese Patent Application Laid-Open No. 2010-270103 and an organic light-emitting device using the compound still have room for improvement from the viewpoint of their commercialization.

The commercialization specifically requires, for example, the following. An optical output with additionally high luminance or additionally high conversion efficiency is needed, and an improvement is needed in terms of durability against, for example, a change over time due to long-term use and deterioration due to an atmospheric gas containing oxygen, moisture, or the like. Further, when its application to a full-color display or the like is assumed, an organic light-emitting device to be used that emits blue light is requested to emit blue light having a good color purity with high efficiency. However, those problems have not yet been sufficiently solved as well.

Therefore, with regard to an organic light-emitting device that emits blue light, an organic light-emitting device having a high color purity, high emission efficiency, and high durability, and a material for realizing the element have been particularly requested.

SUMMARY OF THE INVENTION

The present invention has been made to solve the problems of the prior art. That is, an object of the present invention is to provide a fused polycyclic compound suitable for use mainly as a component for a blue-light-emitting device, and an organic light-emitting device using the compound.

A fused polycyclic compound of the present invention includes a compound represented by at least one of the following general formulae (1), (2), (8), and (9).

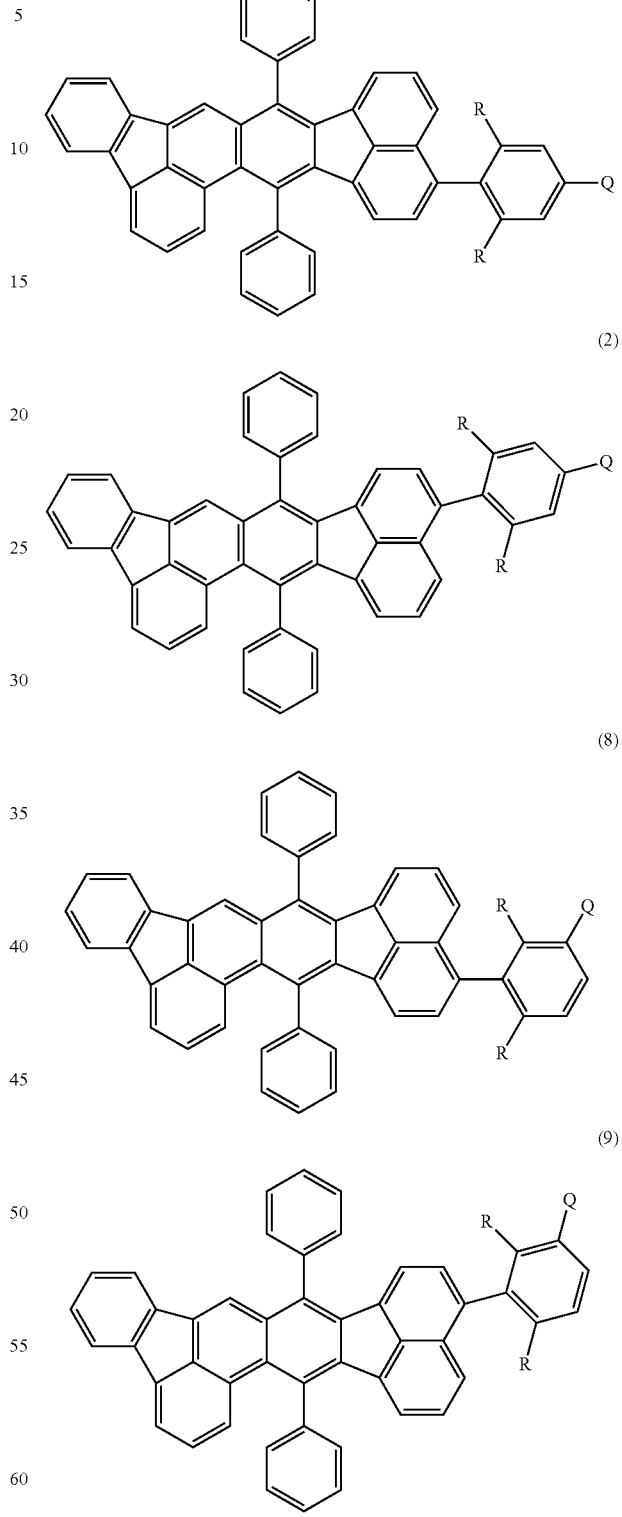

(In the formulae (1), (2), (8), and (9), R represents one of a hydrogen atom and a methyl group, and Q represents an electron-withdrawing substituent selected from the group consisting of the following general formulae (3) to (7).

(3)

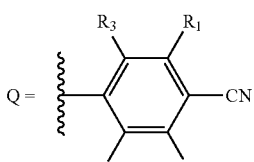

(4)

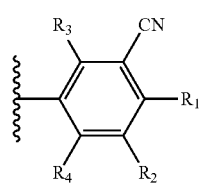

(5)

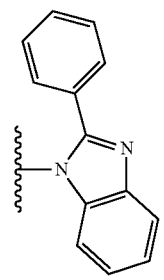

(6)

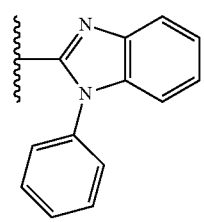

(7)

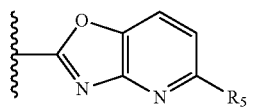

(In the formulae (3) and (4), $R_1$ to $R_4$ each represent a substituent selected from the group consisting of a hydrogen atom, an alkyl group having 1 or more and 4 or less carbon atoms, and a cyano group, and $R_1$ to $R_4$ may be identical to or different from one another, and in the formula (7), $R_5$ represents one of a hydrogen atom and a methyl group.))

The fused polycyclic compound of the present invention shows a high-purity blue luminescent hue having an emission peak at 460 nm or less. In addition, an organic light-emitting device using the fused polycyclic compound of the present invention emits light having high luminance at a low applied voltage and is excellent in durability. Therefore, according to the present invention, it is possible to provide the fused polycyclic compound suitable for use mainly as a component for a blue-light-emitting device, and the organic light-emitting device using the compound.

Further features of the present invention will become apparent from the following description of exemplary embodiments with reference to the attached drawing.

BRIEF DESCRIPTION OF THE DRAWING

FIGURE is a schematic sectional view illustrating an example of a display apparatus having an organic light-emitting device of the present invention and a TFT element as an example of a switching element to be electrically connected to the organic light-emitting device.

DESCRIPTION OF THE EMBODIMENTS

Preferred embodiments of the present invention will now be described in detail in accordance with the accompanying drawings.

An acenaphtho[1,2-k]benzo[e]acephenanthrene derivative as a fused polycyclic compound of the present invention is a compound represented by at least one of the following general formula (1), (2), (8), or (9).

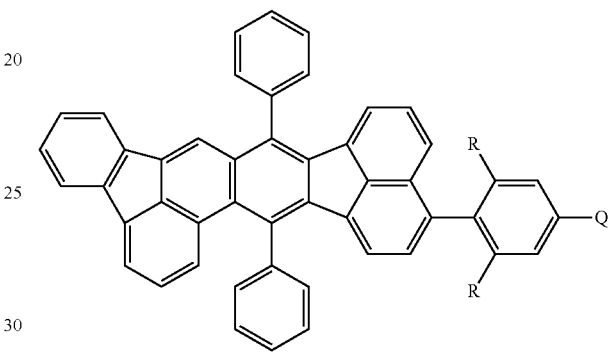

The fused polycyclic compound of the present invention shows a high-purity blue luminescent hue having an emission peak at 460 nm or less.

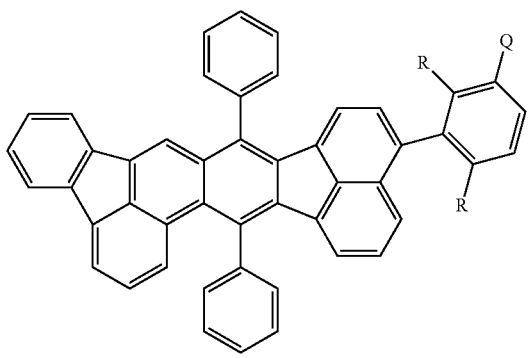

(9)

In the formulae (1), (2), (8), and (9), R represents a hydrogen atom or a methyl group.

In the formulae (1), (2), (8), and (9), Q represents an electron-withdrawing substituent selected from the group consisting of the following general formulae (3) to (7).

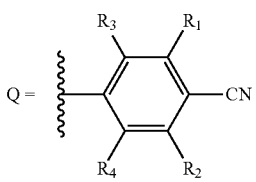

(3)

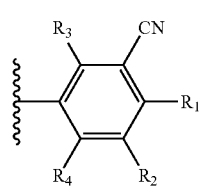

(4)

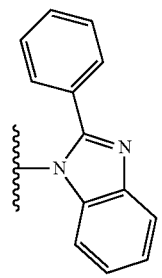

(5)

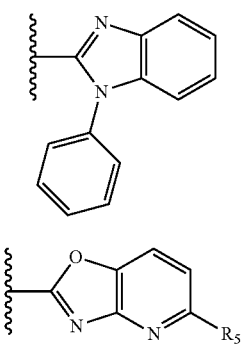

(6)

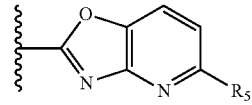

(7)

In the formulae (3) and (4), $R_1$ to $R_4$ each represent a substituent selected from the group consisting of a hydrogen atom, an alkyl group having 1 or more and 4 or less carbon atoms, and a cyano group.

Examples of the alkyl group represented by any one of $R_1$ to $R_4$ include, but of course not limited to, a methyl group, an ethyl group, an n-propyl group, an n-butyl group, an iso-propyl group, an iso-butyl group, an sec-butyl group, a tert-butyl group, a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a cyclopropyl group, and a cyclobutyl group.

It should be noted that $R_1$ to $R_4$ may be identical to or different from one another.

In the formula (7), $R_5$ represents a hydrogen atom or a methyl group.

Here, when the fused polycyclic compound of the present invention is a compound represented by the formula (1) or (2), the compound is preferably a compound represented by the following general formula (10), (11), (30), or (31).

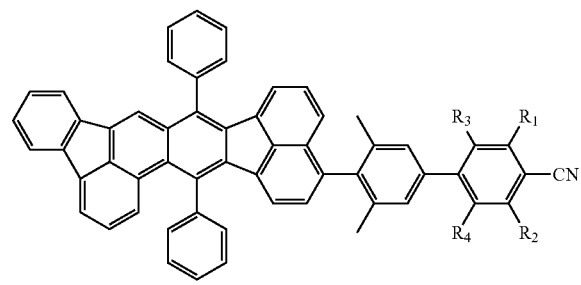

(10)

(11)

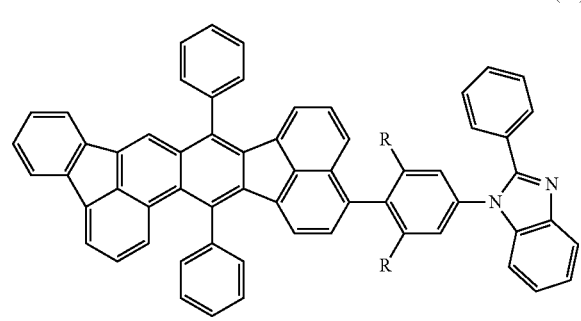

(30)

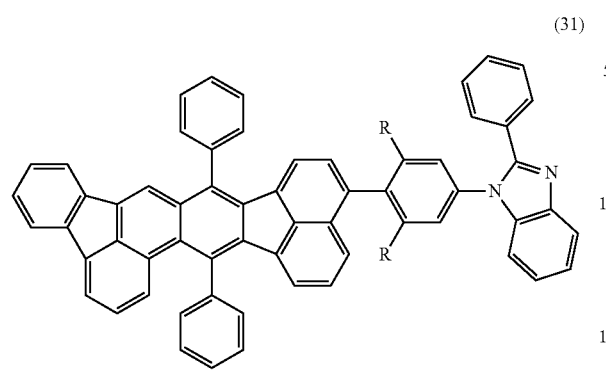

In the formulae (10) and (11), $R_1$ to $R_4$ each represent a substituent selected from the group consisting of a hydrogen atom, an alkyl group having 1 or more and 4 or less carbon atoms, and a cyano group.

Examples of the alkyl group represented by any one of $R_1$ to $R_4$ include, but of course not limited to, a methyl group, an ethyl group, an n-propyl group, an n-butyl group, an iso-propyl group, an iso-butyl group, an sec-butyl group, a tert-butyl group, a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a cyclopropyl group, and a cyclobutyl group.

In the formulae (30) and (31), R represents a hydrogen atom or a methyl group.

On the other hand, when the fused polycyclic compound of the present invention is a compound represented by the formula (8) or (9), the compound is preferably a compound represented by the following general formula (20) or (21).

In the formulae (20) and (21), R represents a hydrogen atom or a methyl group.

(Description of Synthesis Route)

The fused polycyclic compound of the present invention, specifically the compound represented by the general formula (1), (2), (8), or (9) can be synthesized according to, for example, the following synthesis route.

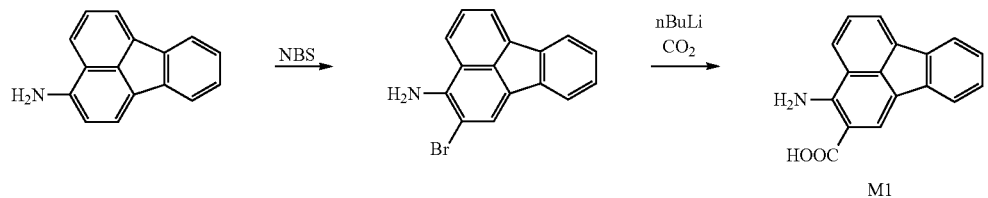

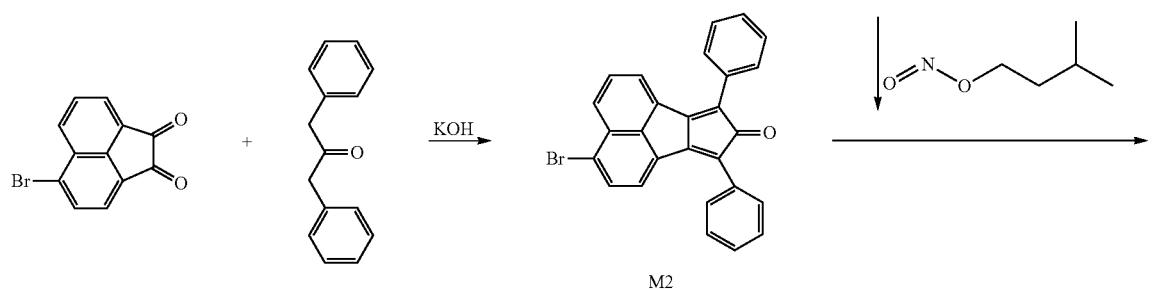

-continued

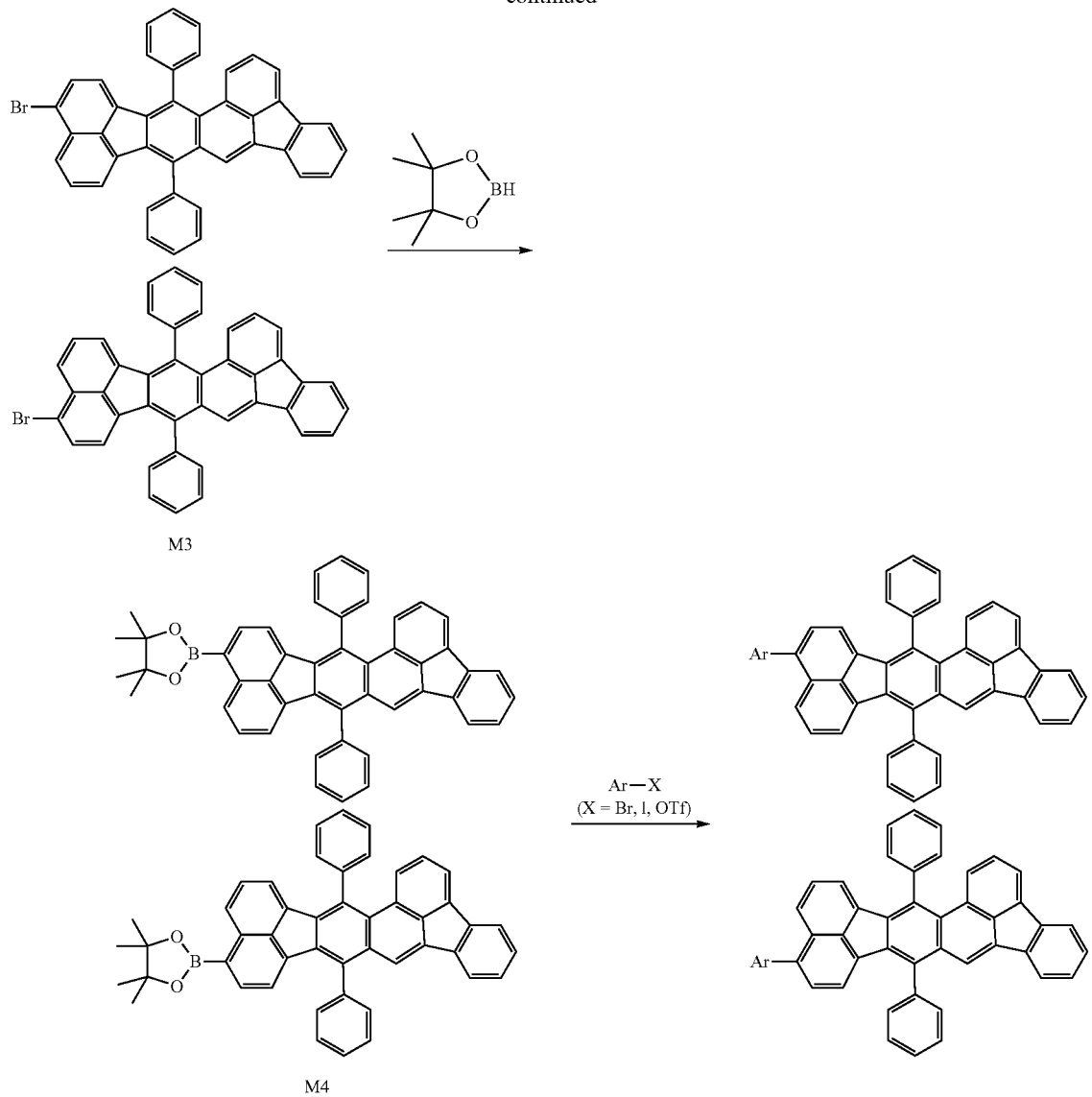

M3

M4

In the synthesis route, two kinds of compounds having a common basic skeleton but different from each other in the substitution position of the substituent Ar are simultaneously obtained. Specifically, a mixture of the compound represented by the formula (1) and the compound represented by the formula (2) or a mixture of the compound represented by the formula (8) and the compound represented by the formula (9) is obtained, provided that in a relationship between the compound represented by the formula (1) and the compound represented by the formula (2) or a relationship between the compound represented by the formula (8) and the compound represented by the formula (9), there arises nearly no difference in emission characteristics between the compounds depending on the substitution position of Ar as long as Ar's are identical to each other. Accordingly, the compounds may be isolated from each other by recrystallization or the like before use, or may be used in a state of the mixture without being treated. In addition, even when the mixture is used without being treated, its emission characteristics do not particularly reduce as compared with that in the case of a single body, and hence its mixing ratio is not particularly limited. In addition, when the compounds are used in the state of the mixture, their crystallinities can be suppressed and hence an effect such as the suppression of concentration quenching can also be expected.

(Discussion on Compound)

Hereinafter, the fused polycyclic compound of the present invention is described in more detail.

In general, in order that the emission efficiency of an organic light-emitting device may be improved, the emission quantum yield of its emission center itself is desirably large. To this end, the following conditions (A) and (B) are required: (A) an oscillator strength is high; and (B) the number of oscillating portions of a skeleton involved in light emission is small.

With regard to the condition (A), an improvement in the symmetry of a skeleton involved in the light emission of a molecule is of importance, provided that no light emission may occur depending on a forbidden transition condition peculiar to a high-symmetry molecule. By the way, a method involving further extending conjugation with the direction in which a conjugate plane is longest as an axis is available as a method of increasing the oscillator strength. When the method is adopted, the dipole moment of the molecule enlarges and hence the oscillator strength increases. In this respect, the fused polycyclic compound of the present invention, in particular, the compound represented by the general formula (1) or (2) has a specific substituent at such a position that a conjugation length further extends with the direction of an acenaphtho[1,2-k]benzo[e]acephenanthrene skeleton in which the conjugate plane is longest as an axis. Performing such molecular design provides a structure in which the oscillator strength of the entire molecule has increased.

With regard to the condition (B), when the skeleton involved in light emission is free of any rotational structure, a reduction in quantum yield due to rotational oscillation can be suppressed. Here, the basic skeleton of the fused polycyclic compound of the present invention is free of any rotational structure. Therefore, a reduction in quantum yield due to rotational oscillation can be suppressed.

Meanwhile, it is important for the emission peak of a material itself, which is one physical property value required for the material to be suitable for blue light emission in an organic EL display, to exist in the range of 430 nm to 480 nm. In particular, an emission peak existing in the range of 440 nm to 460 nm is more preferred for a blue-light-emitting material to have a good color purity.

The basic skeleton which the fused polycyclic compound of the present invention has, that is, the acenaphtho[1,2-k]benzo[e]acephenanthrene skeleton itself has its maximum emission wavelength in a blue region. Accordingly, a compound serving as a blue-light-emitting material having an emission peak at 460 nm or less can be provided by properly selecting the position at which a substituent is introduced into the basic skeleton and the kind of the substituent. Specifically, the fused polycyclic compound represented by the general formula (1), (2), (8), or (9) is a compound obtained by introducing a specific substituent into, as described above, the direction in the basic skeleton in which the conjugate plane is longest, that is, the 12-position or 13-position of the acenaphtho[1,2-k]benzo[e]acephenanthrene skeleton. When a specific substituent, specifically any one of the formulae (3) to (7) is introduced into the 12-position or 13-position, the conjugation length extends and hence the oscillator strength increases. In addition, such molecular structure is designed to satisfy, simultaneously with the foregoing, such a good color purity that an emission wavelength is 460 nm or less so as to be particularly suitable for blue light emission.

Here, the substituent to be introduced into the 12-position or 13-position of the acenaphtho[1,2-k]benzo[e]acephenanthrene skeleton is desirably a substituent selected from the formulae (3) to (7) in order that good blue light emission having an emission peak at 460 nm or less may be output in high quantum yield. A substituent represented by the formula (3) or (4) is particularly preferred.

In addition, the HOMO-LUMO energy levels of the fused polycyclic compound of the present invention are low because the compound has two five-membered ring structures in its skeleton. Here, when an electron-withdrawing substituent, specifically any substituent selected from the formulae (3) to (7) is introduced into the basic skeleton of the fused polycyclic compound of the present invention, the HOMO-LUMO energy levels of the entire molecule thereof become additionally low. Meanwhile, that an oxidation potential becomes lower means that energy needed for oxidation becomes larger. Therefore, the fused polycyclic compound of the present invention is stable against oxidation.

The fused polycyclic compound of the present invention can be used as a component for an organic light-emitting device. When the compound is used as a component for a light-emitting layer (hereinafter referred to as "emission layer") in the element, the compound can be used as a dopant (guest) in the layer. Accordingly, the use of the fused polycyclic compound of the present invention as a component for its emission layer can provide an element having improved emission efficiency, maintaining high luminance for a long time period, and deteriorating owing to energization to a small extent.

In addition, when the emission layer is formed of a host and a guest that are carrier transportable, main processes leading to light emission are formed of the following processes (a) to (d): (a) the transportation of an electron or a hole in the emission layer; (b) the production of an exciton of the host; (c) the transfer of excitation energy between host molecules; and (d) the movement of the excitation energy from the host to the guest.

Desired energy movement in each process and the light emission occur in competition with various deactivation processes.

Needless to say, an improvement in the emission efficiency of an organic light-emitting device requires an increase in the emission quantum yield of its emission center material itself. However, how efficiently energy movement between a host molecule and another host molecule or between the host and the guest can be performed also largely counts. Although a cause for the deterioration of light emission due to energization has not been elucidated at the moment, the deterioration is assumed to be associated with at least the change of an environment surrounding a light emitting material due to the emission center material itself or a peripheral molecule thereof.

In view of the foregoing, the inventors of the present invention have conducted various investigations and have paid attention to an acenaphtho[1,2-k]benzo[e]acephenanthrene derivative represented by any one of the general formulae (1), (2), (8), and (9). Then, the inventors have found that an element using the compound represented by any one of the formulae (1), (2), (8), and (9) as, in particular, a guest for its emission layer emits light with high efficiency, maintains high luminance for a long time period, and deteriorates owing to energization to a small extent.

The fused polycyclic compound according to the present invention is a compound in which an electron-withdrawing substituent selected from the general formulae (3) to (7) is introduced into the 12-position or 13-position of the basic skeleton of acenaphtho[1,2-k]benzo[e]acephenanthrene via a phenyl group. In addition, the compound is a material characterized by its high reduction potential and large electron-accepting property. Here, its electron mobility can be regulated by properly selecting the electron-withdrawing substituent represented by any one of the general formulae (3) to (7) to control the reduction potential. Thus, the inventors of the present invention have found that a combination of the compound with any one of the various hosts enables the element to be driven at a low voltage, to maintain high luminance for a long time period, and to be reduced in the extent of deterioration due to energization.

The present invention has been made by performing molecular design based on the foregoing discussion.

Hereinafter, specific examples of the acenaphtho[1,2-k]benzo[e]acephenanthrene derivative as the fused polycyclic compound of the present invention are shown, provided that these merely show specific examples and the present invention is not limited thereto.

(1) Compound Example 1
group of compounds each represented by the following general formula (10) or (11).
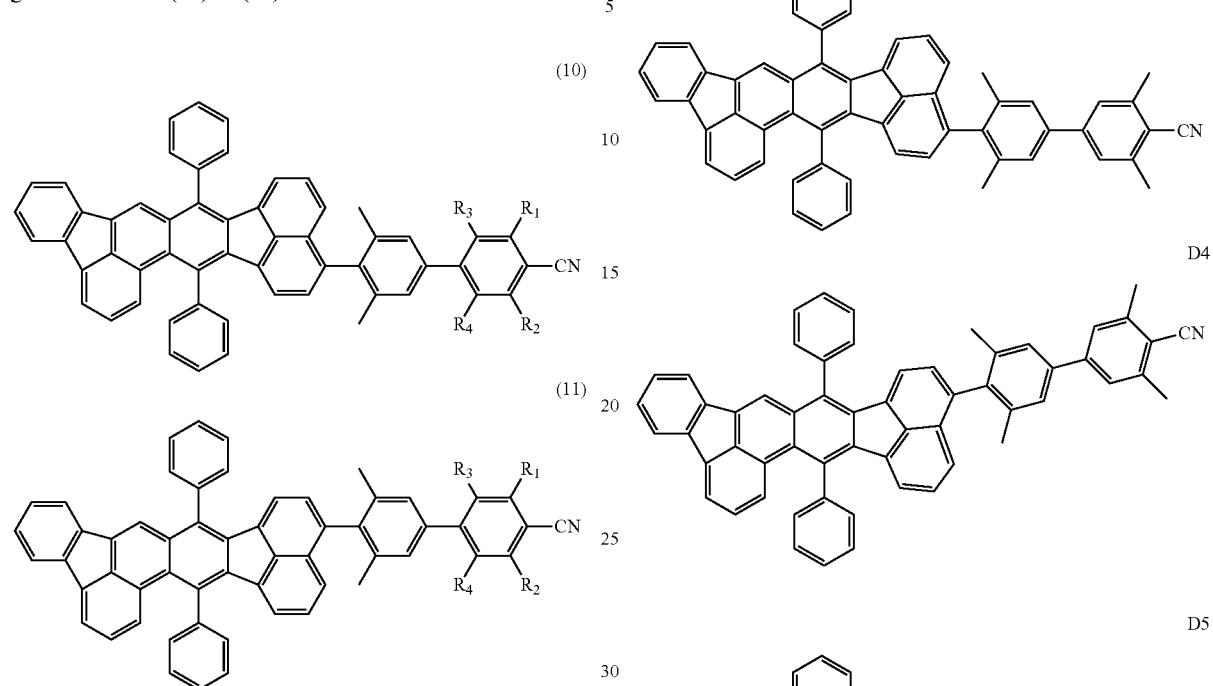
(In the formulae (10) and (11), $R_1$ to $R_4$ each represent a hydrogen atom, an alkyl group having 1 or more and 4 or less carbon atoms such as a methyl group or a trifluoromethyl group, or a cyano group.)
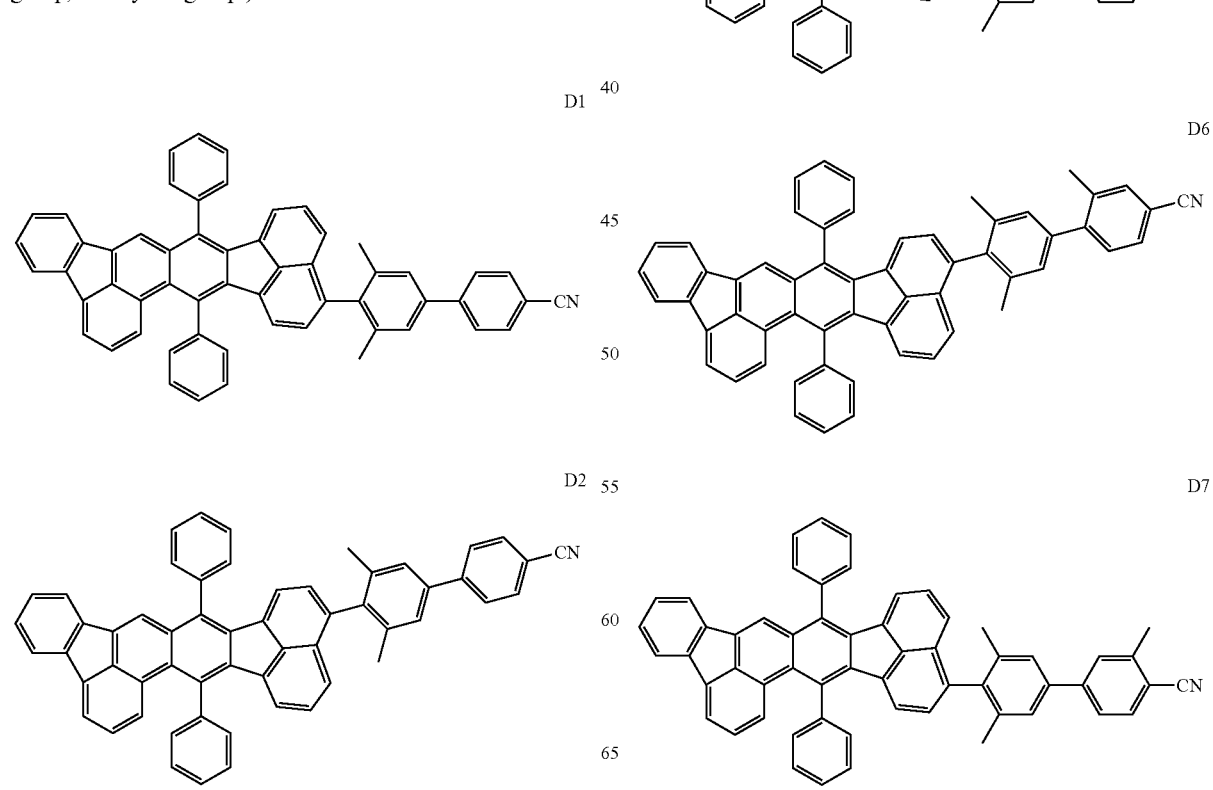

-continued
D8
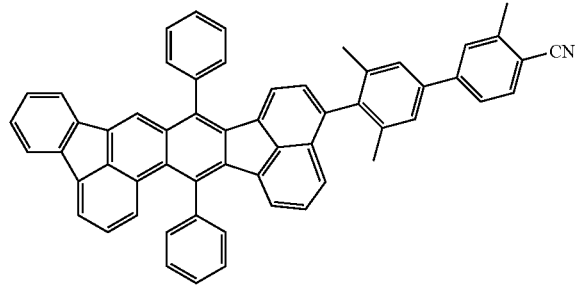
D9
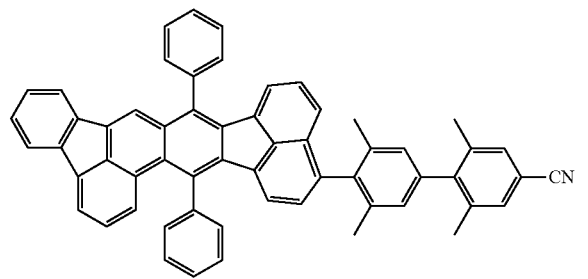
D10
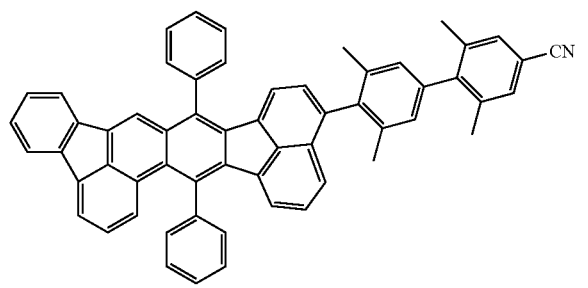
D11
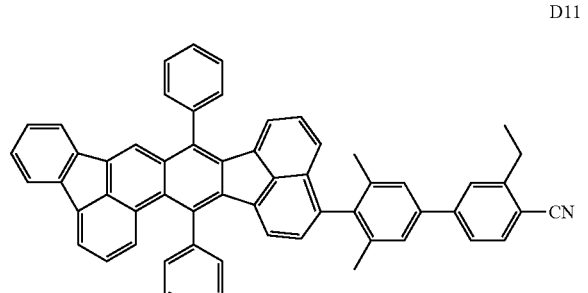
D12
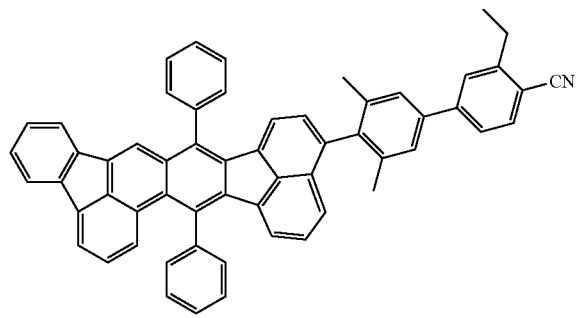
-continued
D13
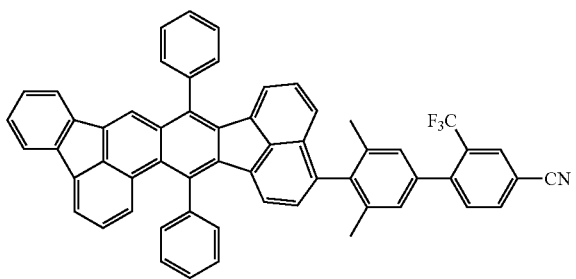
D14
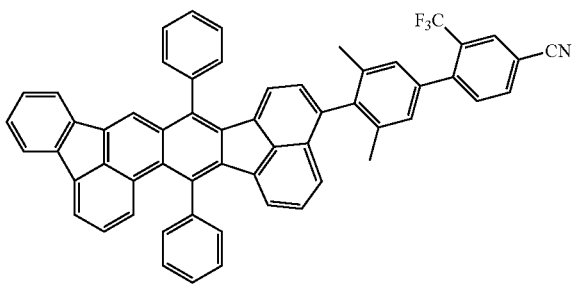
D15
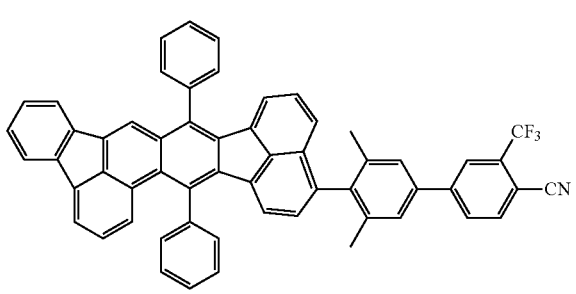
D16
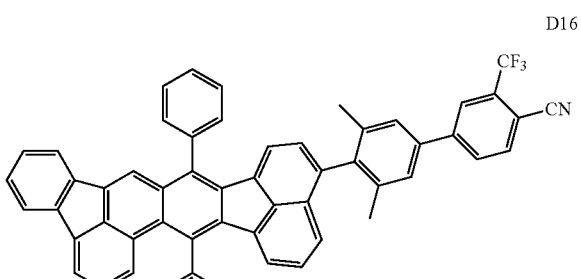
D17
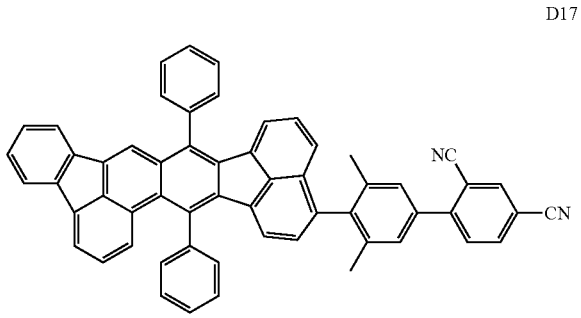

-continued
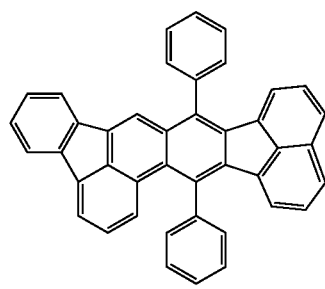
D18
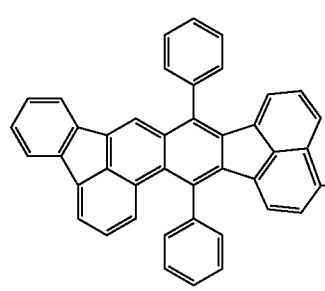
D19
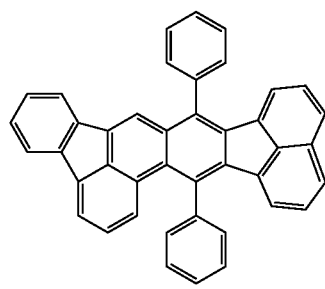
D20
(2) Compound Example 2
group of compounds each represented by the following general formula (12) or (13).
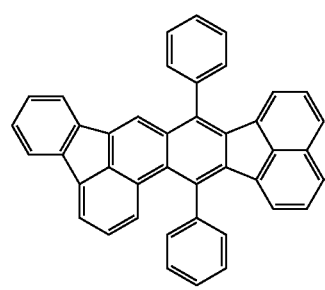
(12)
-continued
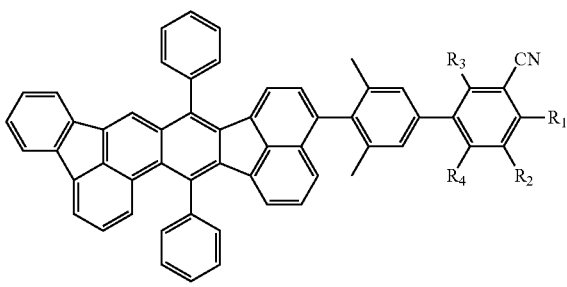
(13)
(In the formulae (12) and (13), $R_1$ to $R_4$ each represent a hydrogen atom, an alkyl group having 1 or more and 4 or less carbon atoms such as a methyl group or a trifluoromethyl group, or a cyano group.)
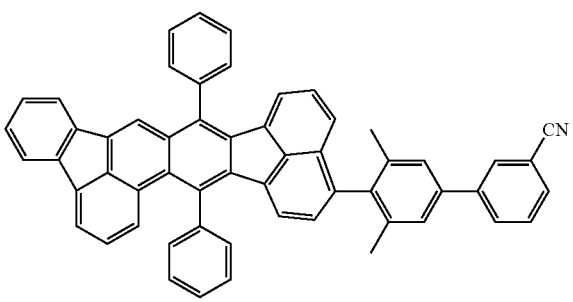
D21
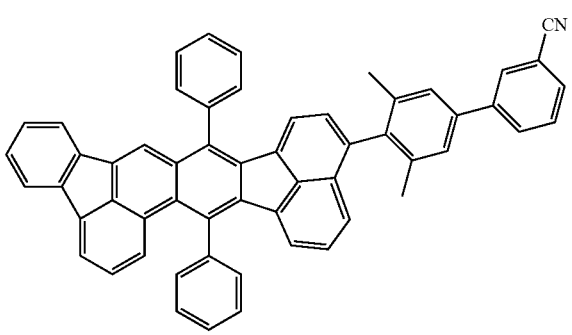
D22
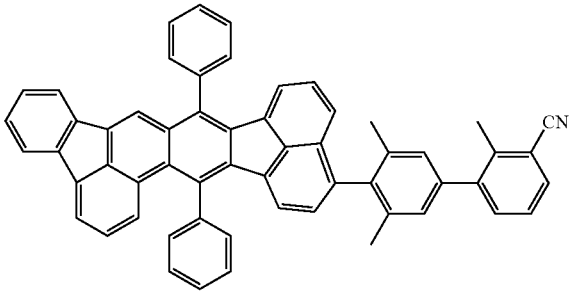
D23

D24
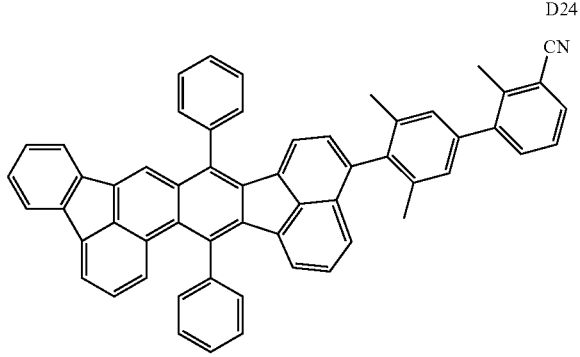
D25
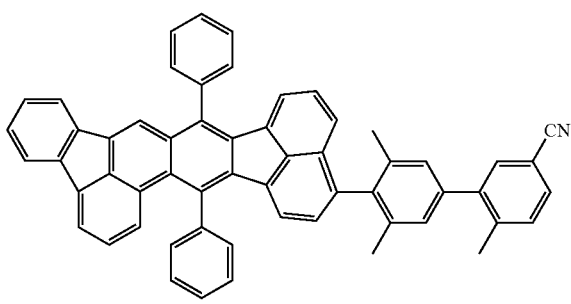
D26
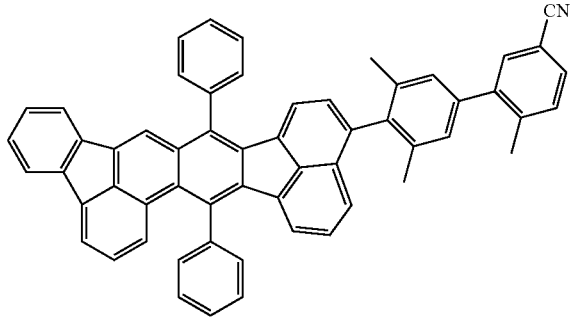
D27
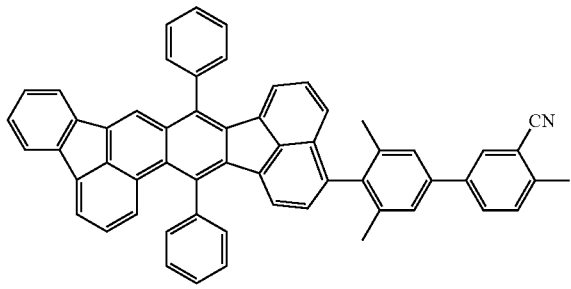
D28
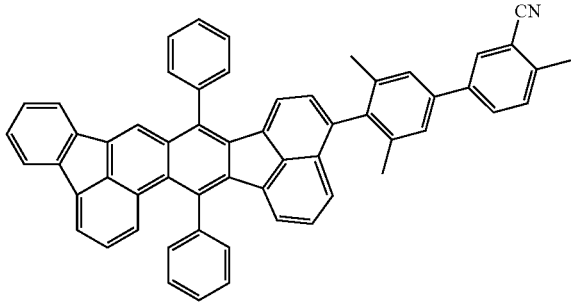
D29
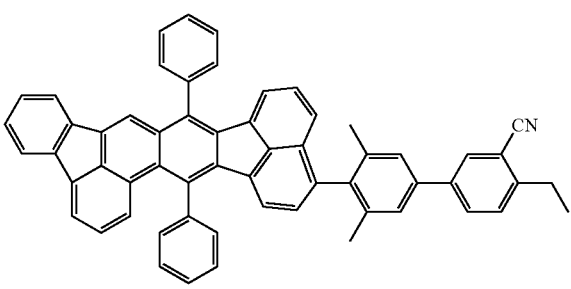
D30
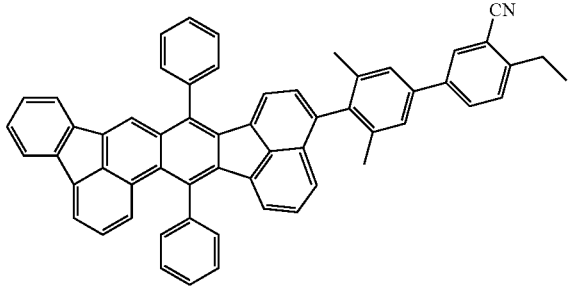
D31
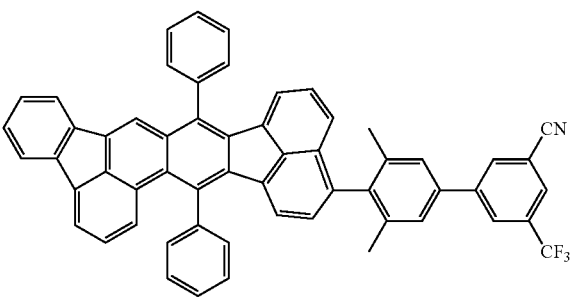
D32
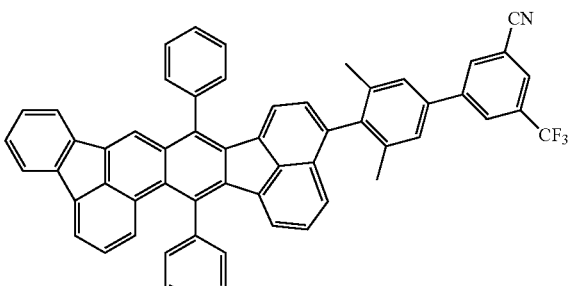
D33
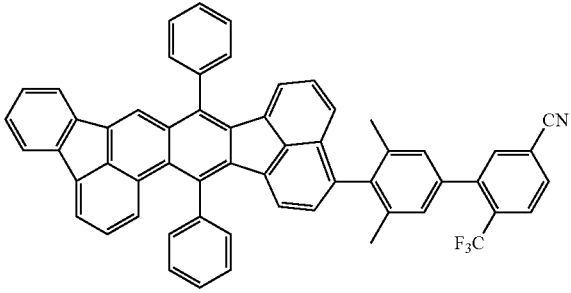

-continued
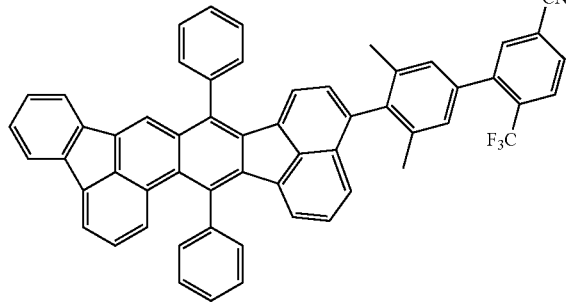
D34
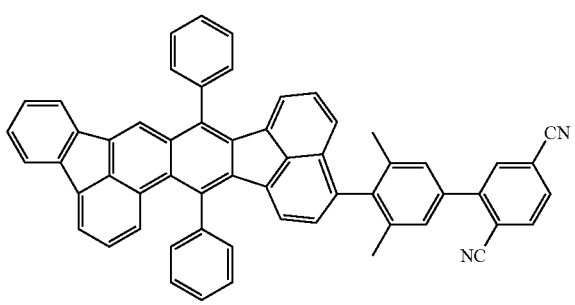
D35
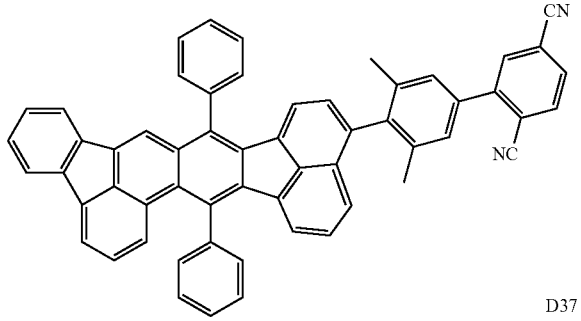
D36
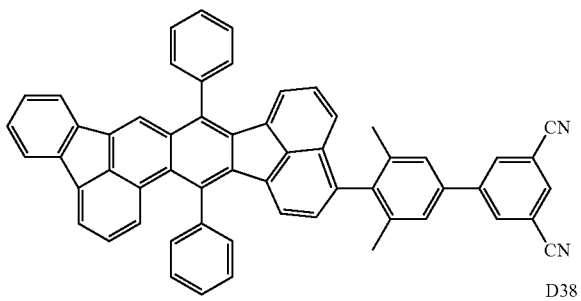
D37
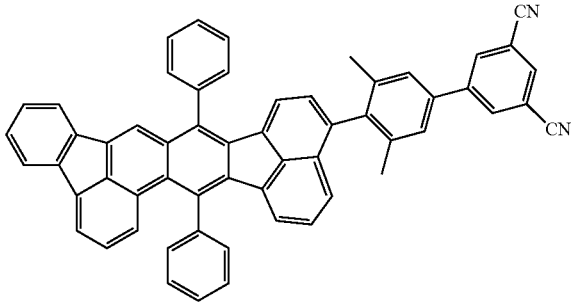
D38
(3) Compound Example 3
group of compounds each represented by the following general formula (14) or (15).
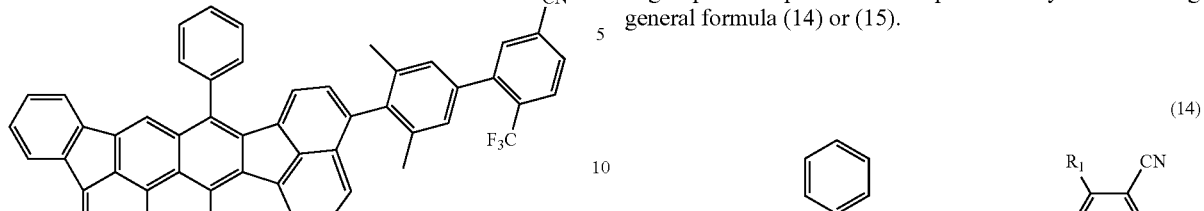
(14)
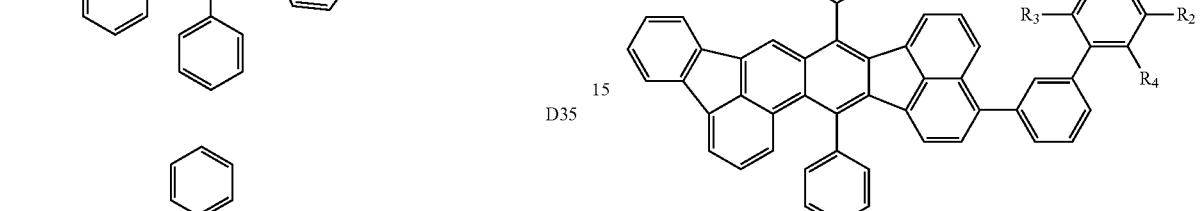
(15)
(In the formulae (14) and (15), $R_1$ to $R_4$ each represent a hydrogen atom, an alkyl group having 1 or more and 4 or less carbon atoms such as a methyl group or a trifluoromethyl group, or a cyano group.)
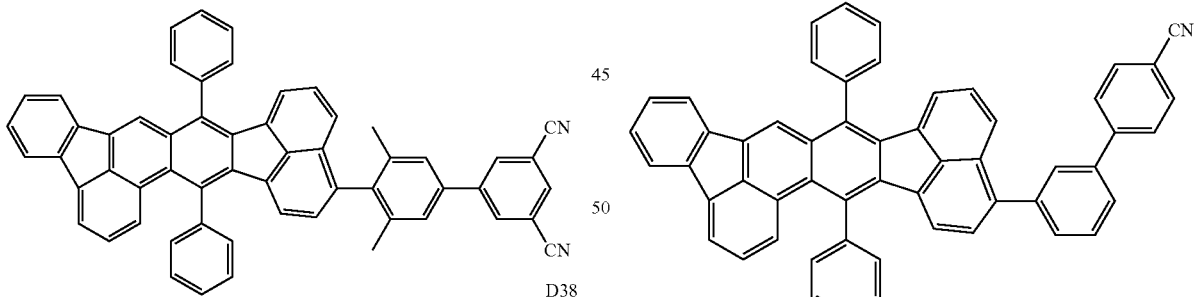
D39
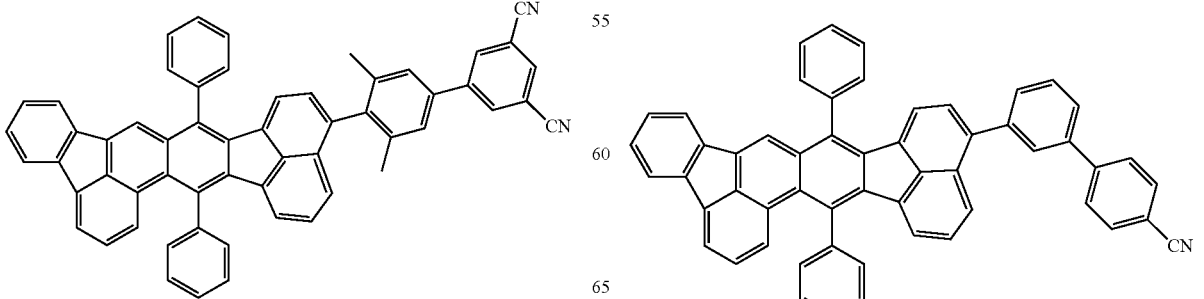
D40

D41
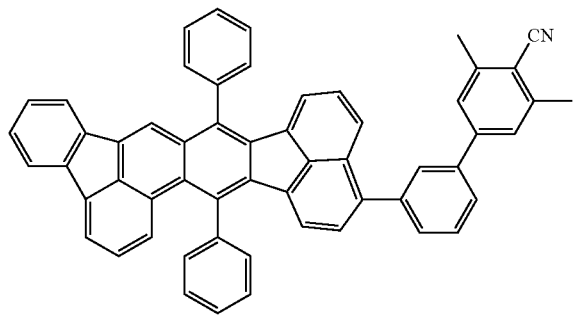
D46
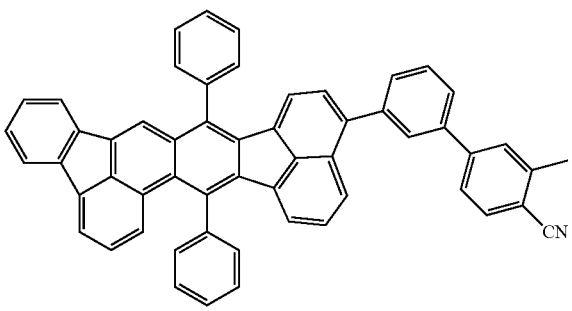
D42
D43
D44
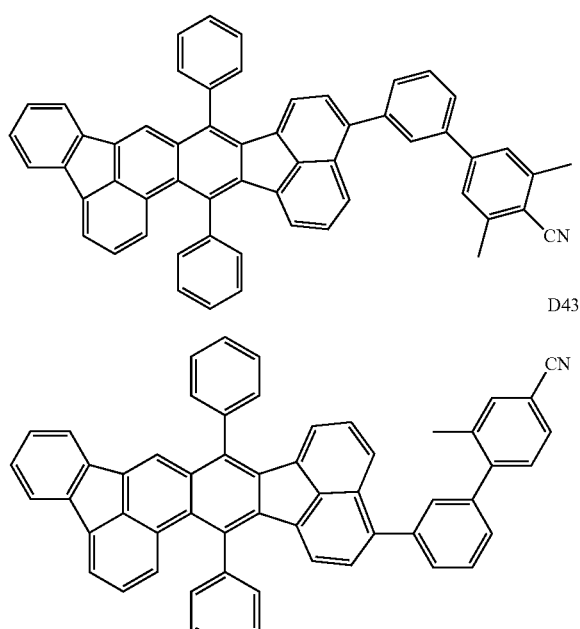
D47
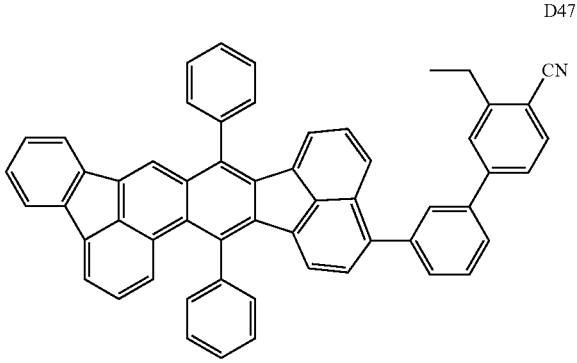
D48
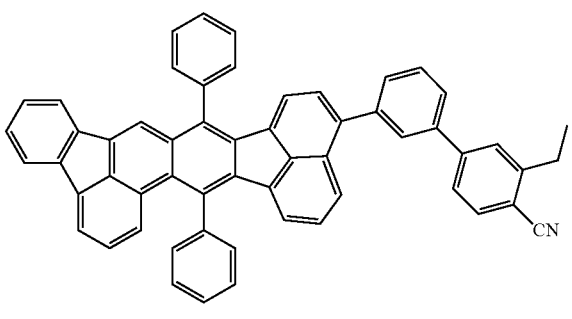
D45
D49
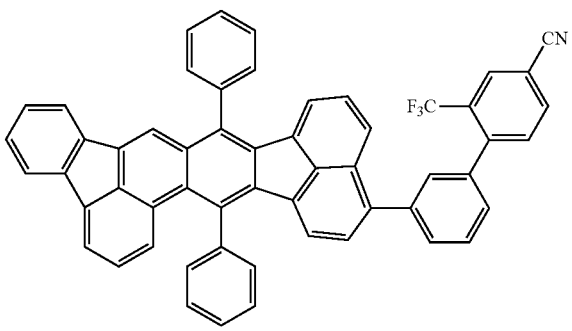

D50
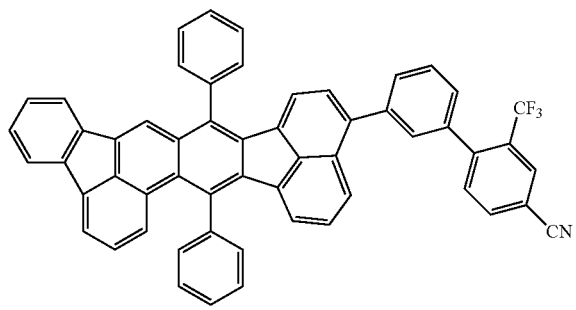
D51
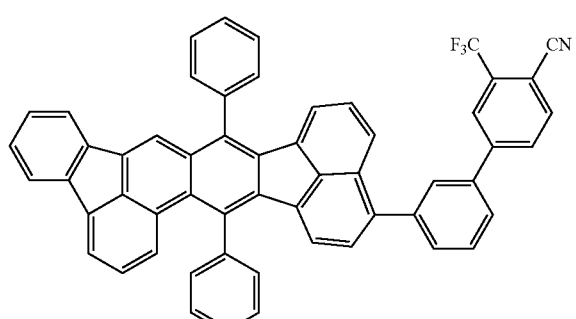
D52
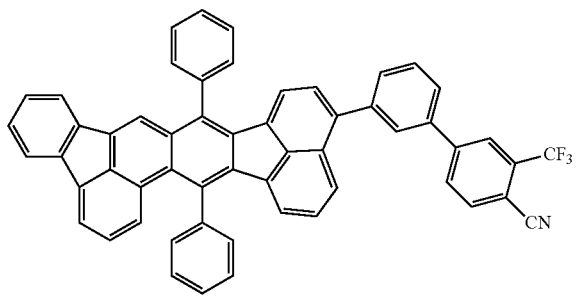
D53
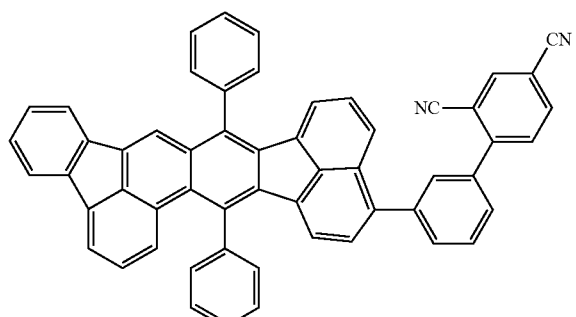
D54
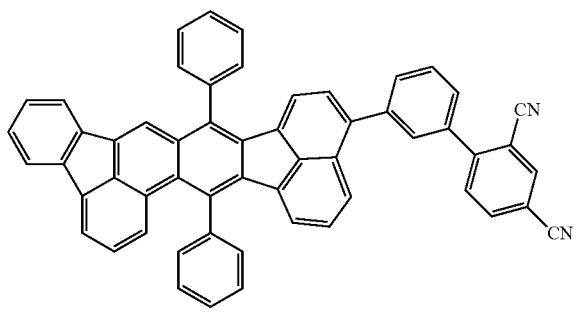
D55
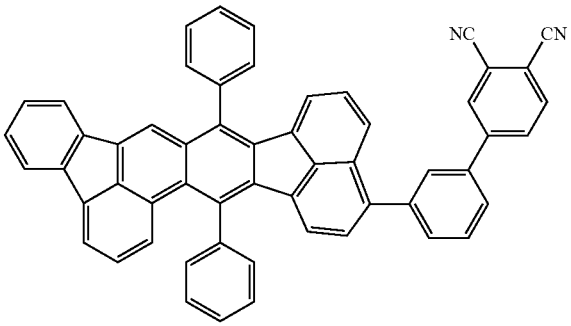
D56
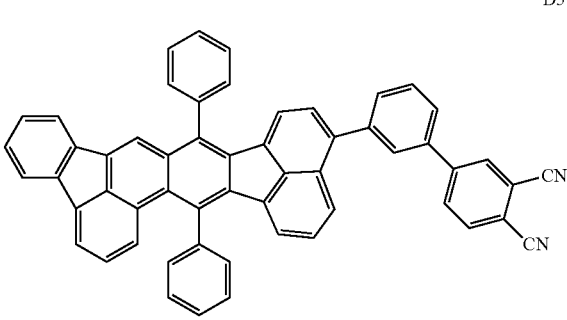
(4) Compound Example 4
group of compounds each represented by the following general formula (16) or (17).
(16)
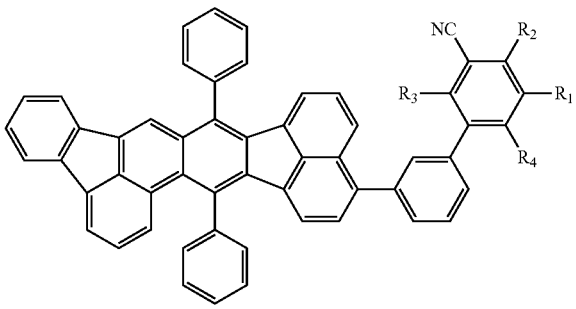
(17)
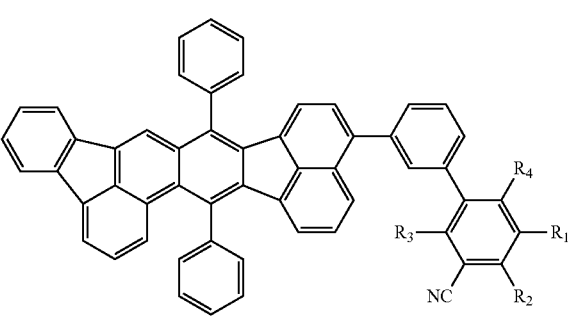
(In the formulae (16) and (17), $R_1$ to $R_4$ each represent a hydrogen atom, an alkyl group having 1 or more and 4 or less carbon atoms such as a methyl group or a trifluoromethyl group, or a cyano group.)

-continued
D57
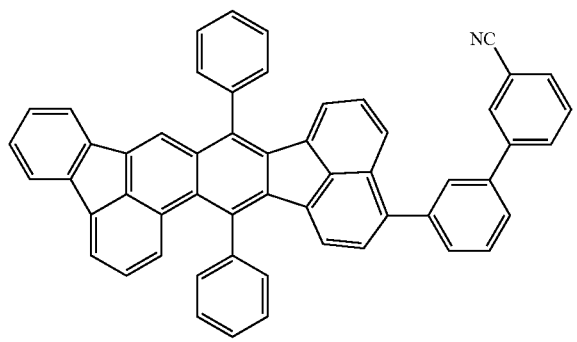
D58
D59
D60
D61
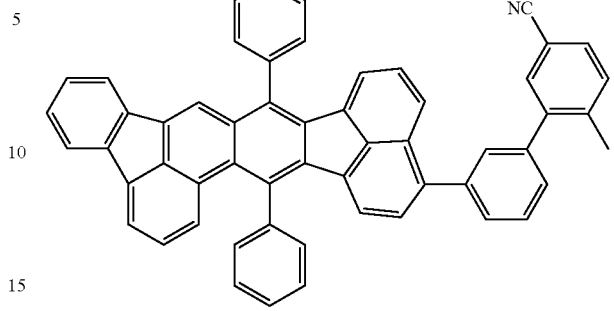
D62
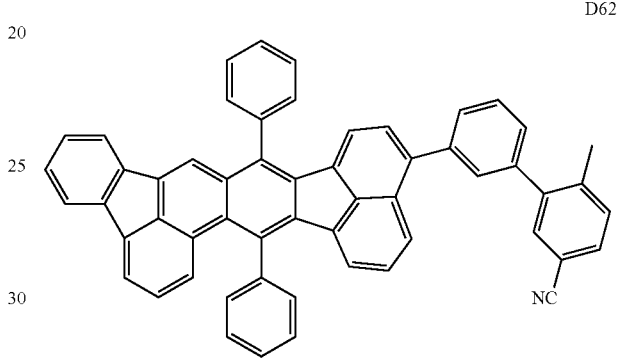
D63
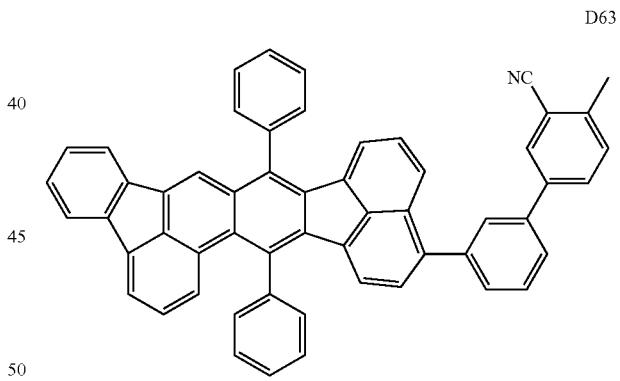
D64
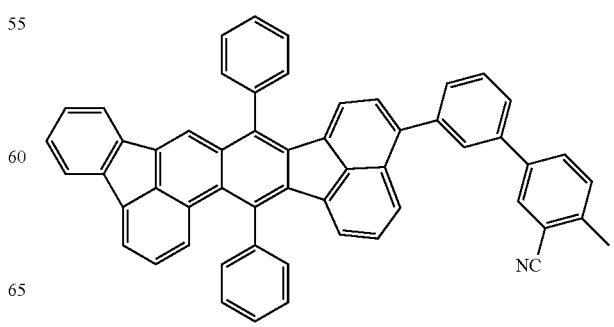

D65
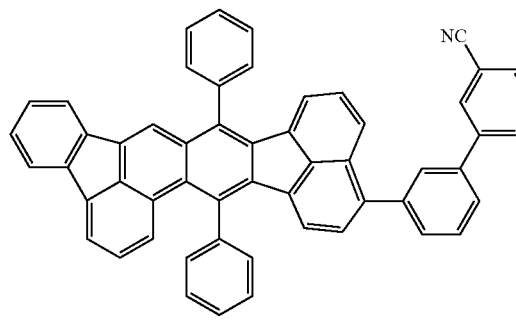
D66
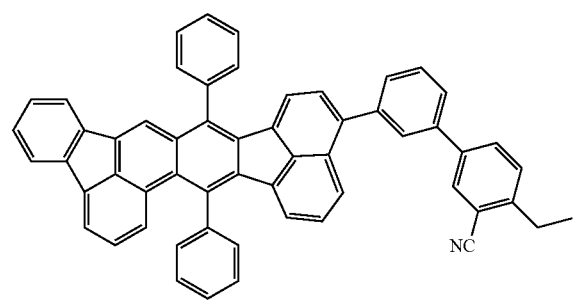
D67
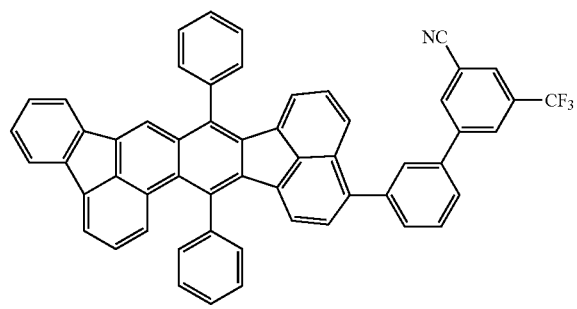
D68
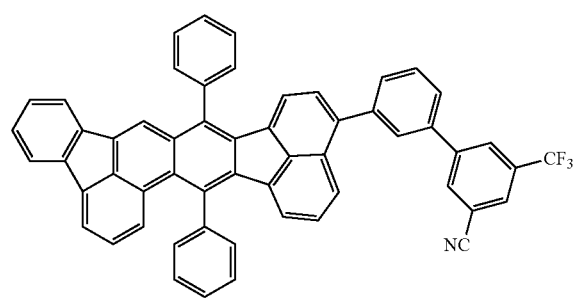
D69
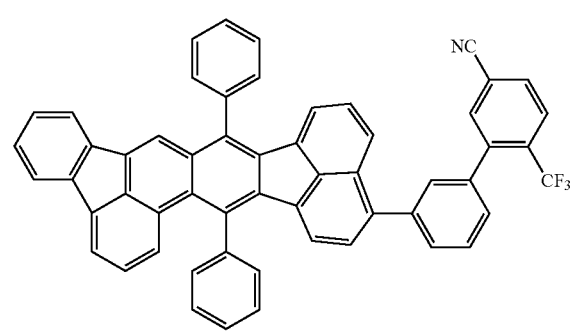
D70
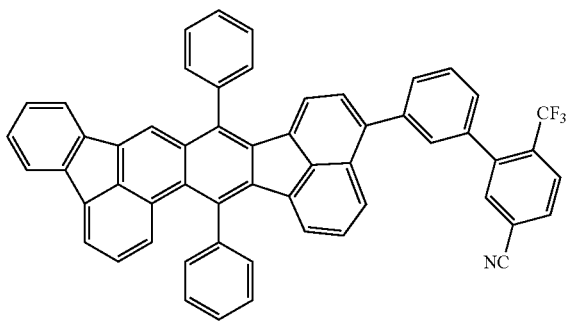
D71
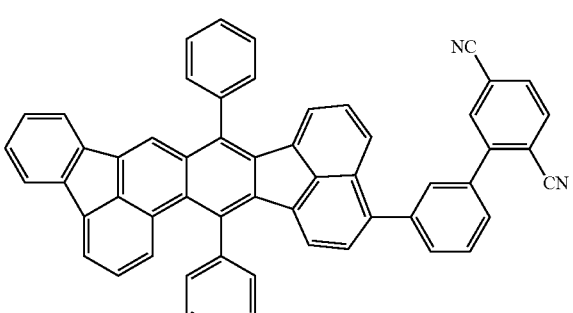
D72
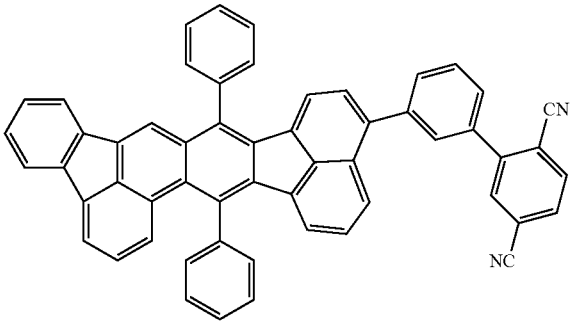
D73
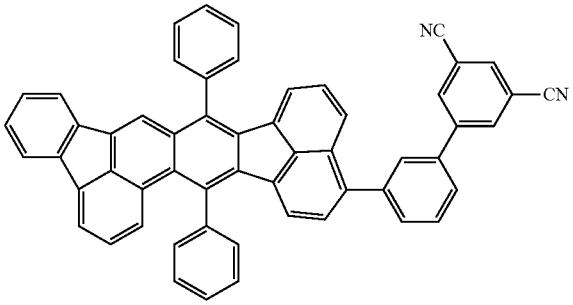

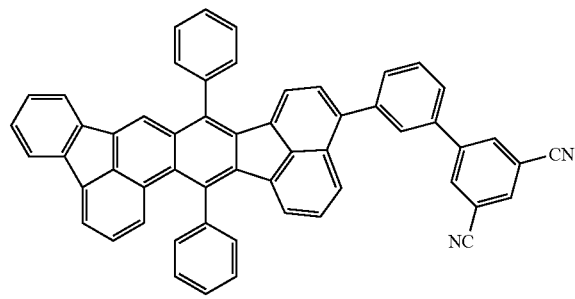
D74
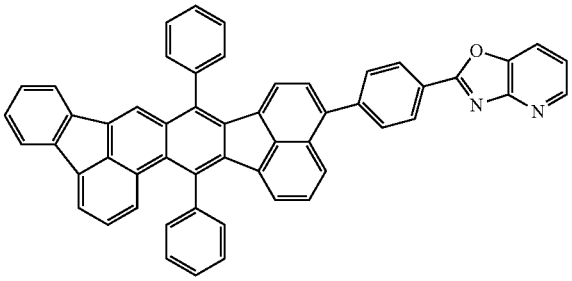
D76
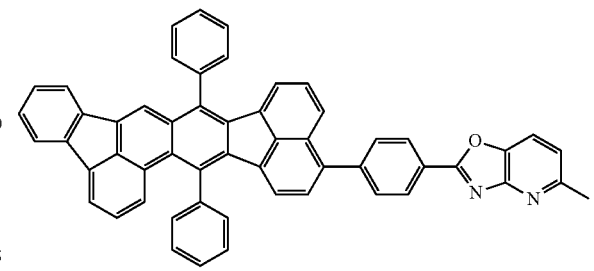
D77
(5) Compound Example 5
group of compounds each represented by the following general formula (18) or (19).
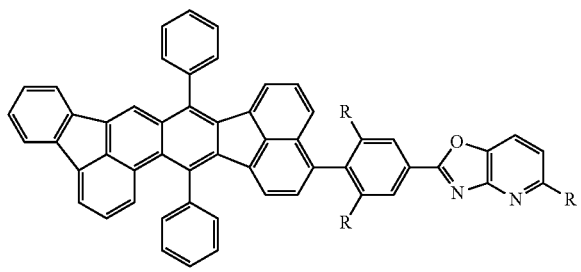
(18)
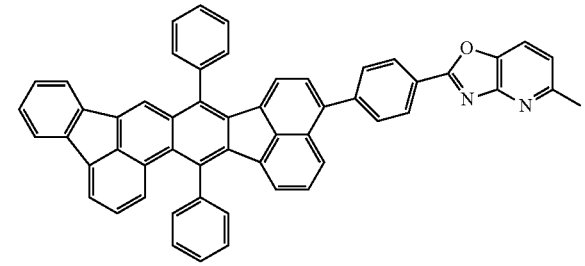
D78
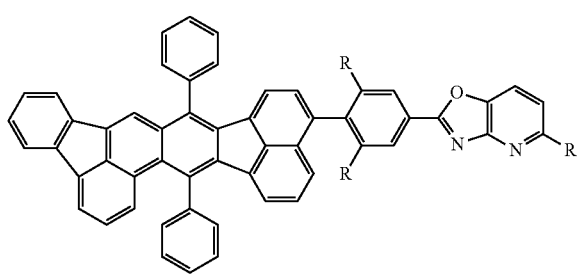
(19)
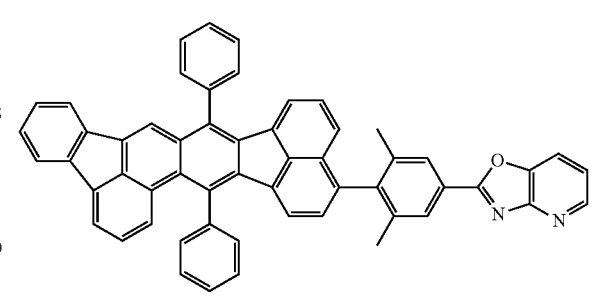
D79
(In the formulae (18) and (19), R represents a hydrogen atom or a methyl group.)
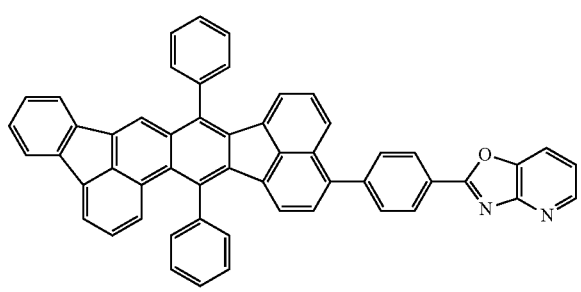
D75
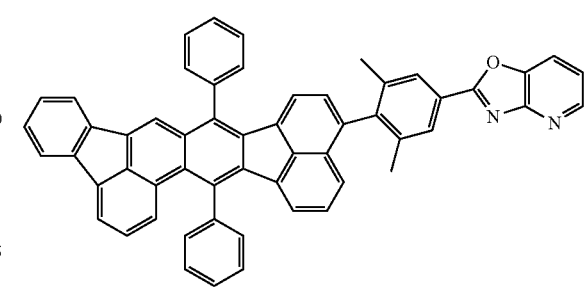
D80

-continued
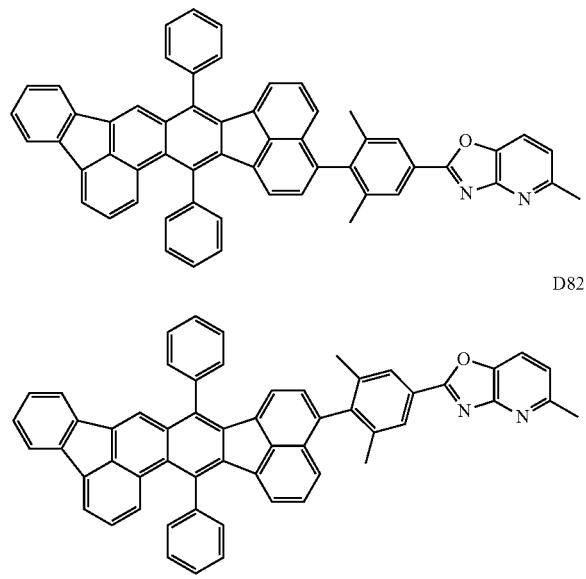
(6) Compound Example 6
group of compounds each represented by the following general formula (20) or (21).
(20)
(21)
(In the formulae (20) and (21), R represents a hydrogen atom or a methyl group.)
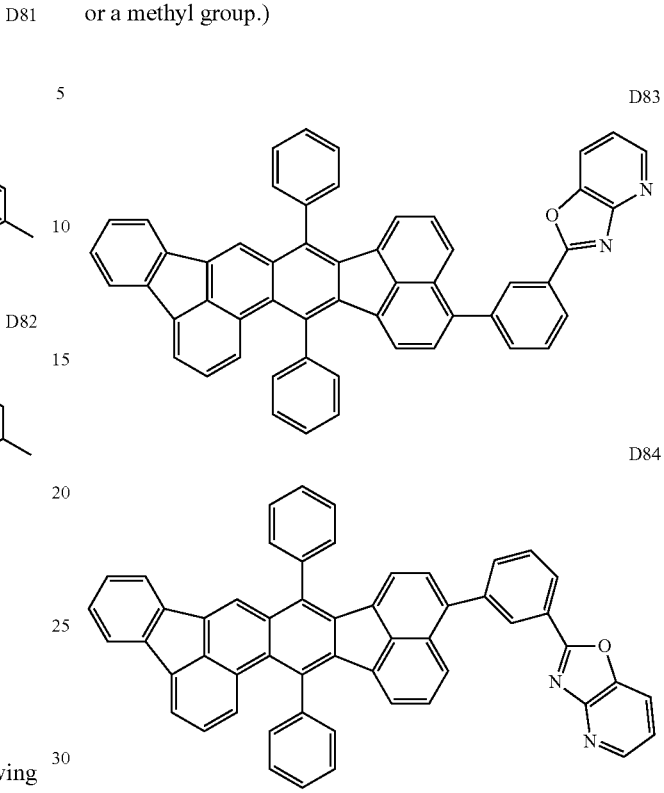
(7) Compound Example 7
group of compounds each represented by the following general formula (1) or (2), in which Q in the formulae (1) and (2) is a substituent represented by the following general formula (5) or (6).

(1)
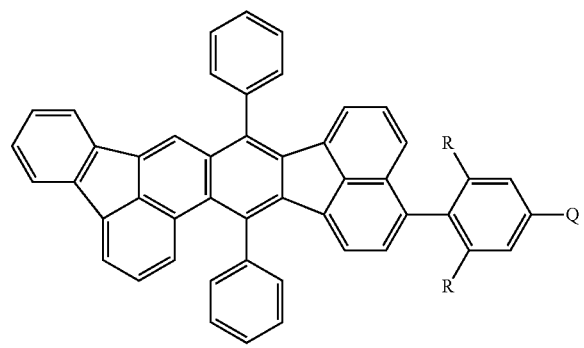
(2)
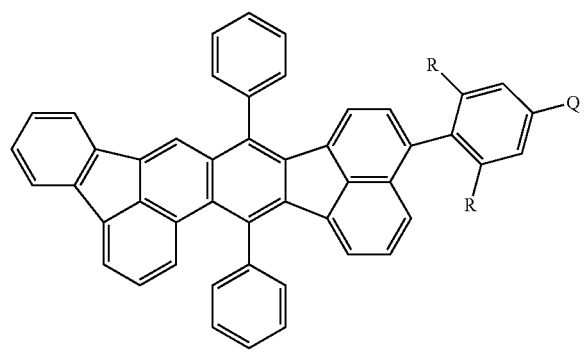
(5)
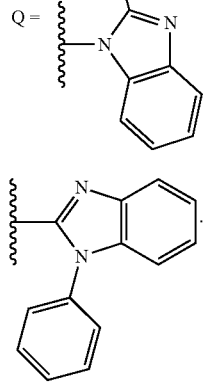
(6)
(In the formulae (1), (2), (5), and (6), R represents a hydrogen atom or a methyl group.)
D87
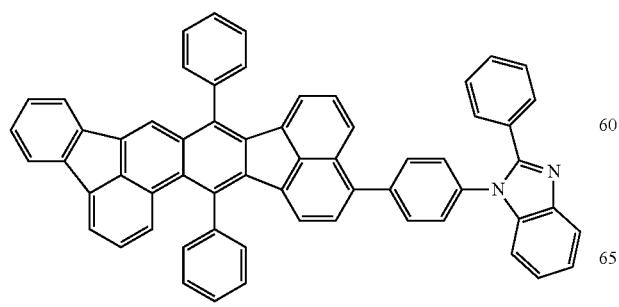
D88
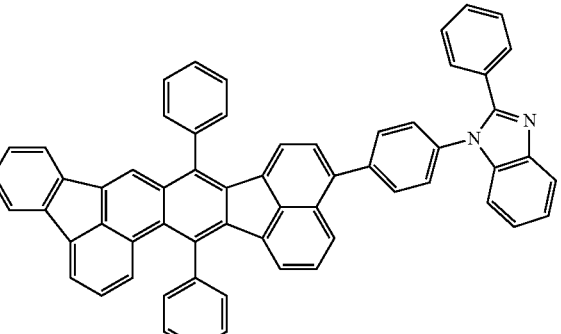
D89
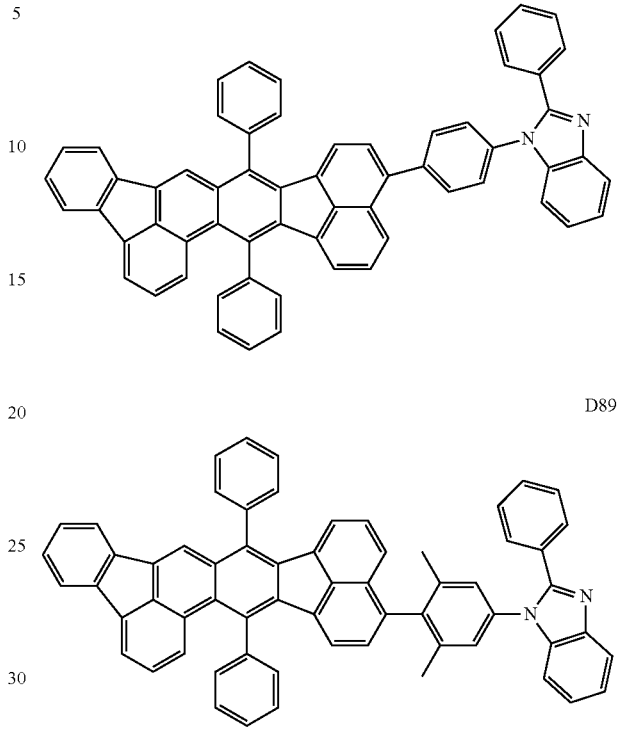
D90
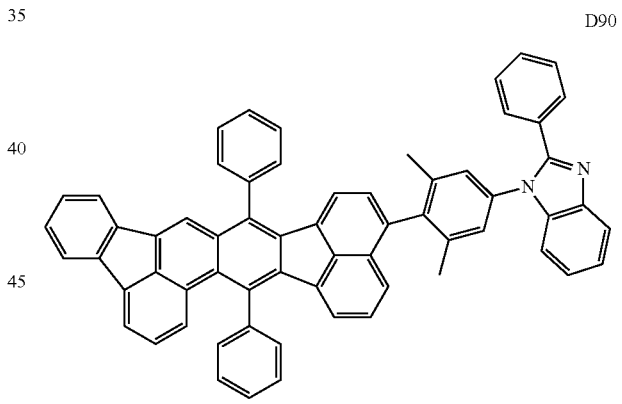
D91
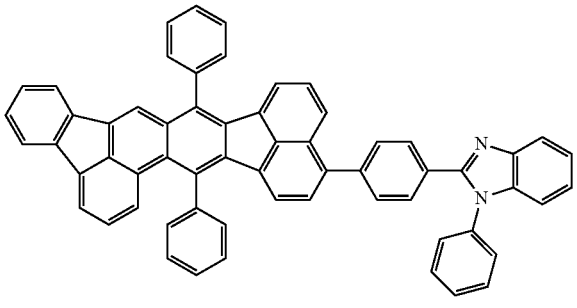

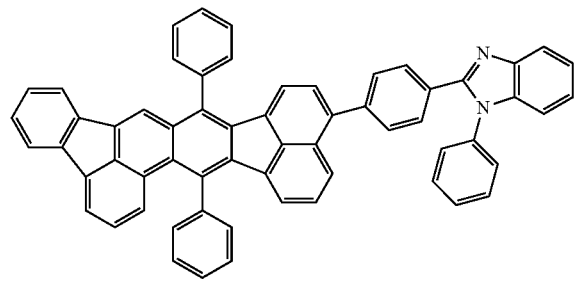
D92
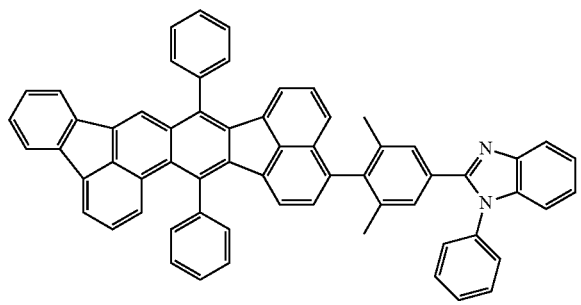
D93
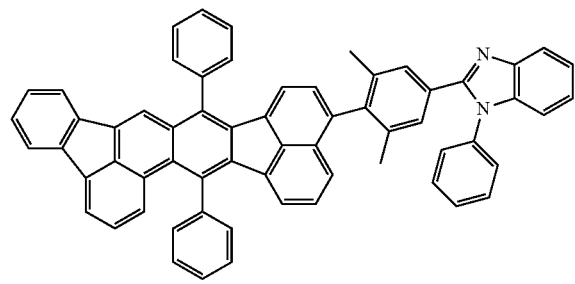
D94
(8) Compound Example 8
group of compounds each represented by the following general formula (22) or (23), in which Q in the formulae (22) and (23) is a substituent represented by the following general formula (5) or (6).
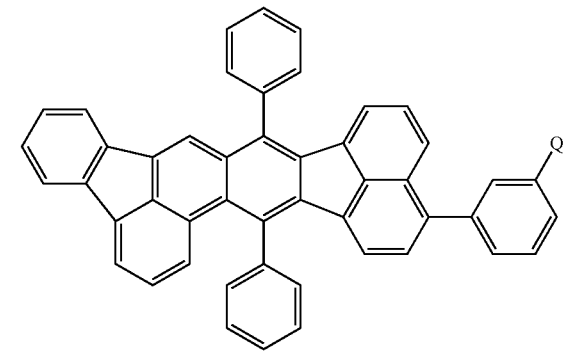
(22)
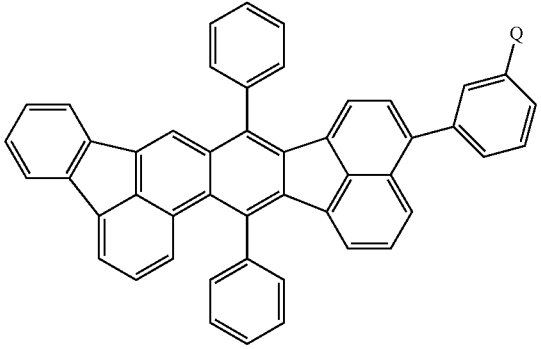
(23)
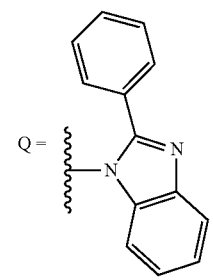
Q = (5)
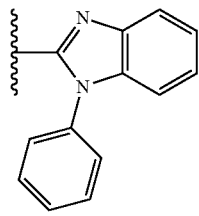
(6)
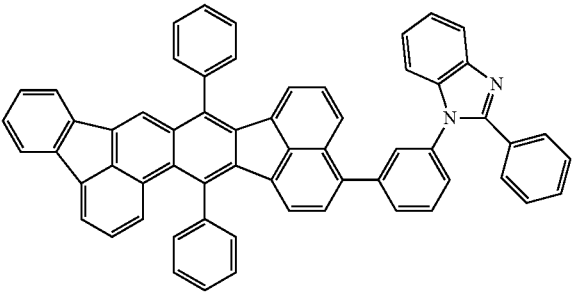
D95
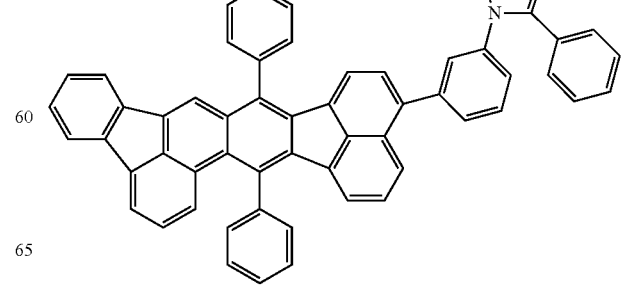
D96

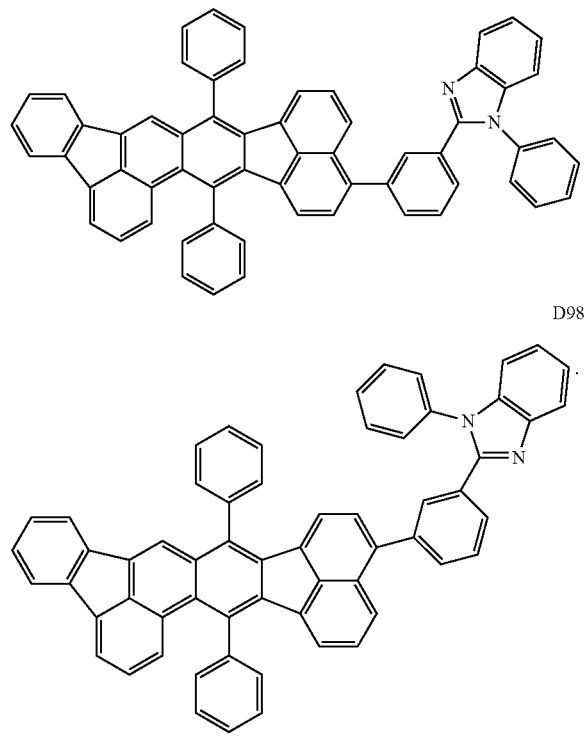

(Description of Organic Light-Emitting Device)

Next, an organic light-emitting device of the present invention is described.

The organic light-emitting device of the present invention has a pair of electrodes, an anode and a cathode, and an organic compound layer disposed between the anode and the cathode. Here, the organic compound layer is a single layer or a stack formed of multiple layers, and in the present invention, at least one layer constituting the organic compound layer has the fused polycyclic compound according to the present invention.

The organic compound layer constituting the organic light-emitting device of the present invention is a single layer, or a stack formed of multiple layers, including at least an emission layer. When the organic compound layer is a stack constituted of multiple layers, the organic compound layer is a stack having any one of, for example, a hole injection layer, a hole transport layer, a hole/exciton blocking layer, an electron transport layer, and an electron injection layer as well as the emission layer.

Specific examples of the organic light-emitting device of the present invention are described below: (i) (anode/)emission layer(/cathode); (ii) (anode/)hole transport layer/electron transport layer(/cathode); (iii) (anode/)hole transport layer/emission layer/electron transport layer(/cathode); (iv) (anode/)hole injection layer/hole transport layer/emission layer/electron transport layer(/cathode); and (v) (anode/)hole transport layer/emission layer/hole-exciton blocking layer/electron transport layer(/cathode).

It should be noted that the foregoing constructions (i) to (v) merely show specific examples of a very basic element construction, and the construction of the organic compound layer in the organic light-emitting device of the present invention is not limited thereto.

In the organic light-emitting device of the present invention, the fused polycyclic compound of the present invention is incorporated into any layer constituting the organic compound layer. Specifically, the compound is incorporated into, for example, the hole injection layer, the hole transport layer, the emission layer, the hole/exciton blocking layer, or the electron transport layer. The compound is preferably incorporated into the emission layer.

Here, when the fused polycyclic compound of the present invention is incorporated into the emission layer, the emission layer may be constituted only of the fused polycyclic compound of the present invention, or may be constituted of a host and a guest. In addition, when the emission layer is constituted of the host and the guest, the fused polycyclic compound of the present invention can be used as the guest.

Here, when the fused polycyclic compound of the present invention is used as the guest, the concentration of the guest to the host is preferably 0.1 wt % or more and 30 wt % or less, more preferably 0.5 wt % or more and 10 wt % or less.

In the organic light-emitting device of the present invention, in addition to the fused polycyclic compound of the present invention, as necessary, hitherto known low-molecular and high-molecular materials may be used. Specifically, a hole injecting material, a hole transporting material, a host, an electron injecting material, an electron transporting material, and the like may be used as components in combination with the fused polycyclic compound of the present invention.

Specific examples of those materials are given below.

The hole injecting material or the hole transporting material is preferably a material having a high hole mobility. Low-molecular and high-molecular materials each having hole injecting performance or hole transporting performance are exemplified by, but of course not limited to, a triarylamine derivative, a phenylenediamine derivative, a stilbene derivative, a phthalocyanine derivative, a porphyrin derivative, poly(vinylcarbazole), poly(thiophene), and other conductive polymers.

Examples of the host include, but of course not limited to, a triarylamine derivative, a phenylene derivative, a fused ring aromatic compound (e.g., a naphthalene derivative, a phenanthrene derivative, a fluorene derivative, a chrysene derivative, an anthracene derivative, or a pyrene derivative), an organic metal complex (e.g., an organic aluminum complex such as tris(8-quinolinolato)aluminum, an organic beryllium complex, an organic iridium complex, or an organic platinum complex), and a polymer derivative such as a poly(phenylenevinylene) derivative, a poly(fluorene) derivative, a poly(phenylene) derivative, a poly(thienylenevinylene) derivative, or a poly(acetylene) derivative.

The electron injecting material or the electron transporting material is selected in consideration of, for example, a balance with the hole mobility of the hole injecting material or the hole transporting material. A material having electron injecting performance or electron transporting performance is exemplified by, but of course not limited to, an oxadiazole derivative, an oxazole derivative, a pyrazine derivative, a triazole derivative, a triazine derivative, a quinoline derivative, a quinoxaline derivative, a phenanthroline derivative, and an organic aluminum complex.

Next, components for the members excluding the organic compound layer are described.

It is recommended that a component for an anode have as large a work function as possible. Examples thereof include metal elements such as gold, platinum, silver, copper, nickel, palladium, cobalt, selenium, vanadium, and tungsten, or alloys including combinations of multiple kinds of those metal elements, and metal oxides such as tin oxide, zinc oxide, indium oxide, indium tin oxide (ITO), and indium zinc oxide. Further, conductive polymers such as polyaniline, polypyrrole, and polythiophene may also be used. One kind of those electrode substances may be used alone, or multiple kinds thereof may be used in combination. Further, the anode may be constructed of a single layer or may be constructed of multiple layers.

Meanwhile, it is recommended that a component for a cathode have a small work function. Examples of the material include alkali metals such as lithium, alkaline earth metals such as calcium, and metal elements such as aluminum, titanium, manganese, silver, lead, and chromium. Alternatively, alloys including combinations of multiple kinds of those metal elements may also be used. For example, magnesium-silver, aluminum-lithium, aluminum-magnesium, and the like may be used. Metal oxides such as indium tin oxide (ITO) may also be utilized. One kind of those electrode substances may be used alone, or two or more kinds thereof may be used in combination. Further, the cathode may be constructed of a single layer or may be constructed of multiple layers.

In the organic light-emitting device of the present invention, a layer including the fused polycyclic compound of the present invention and any other layer formed of an organic compound are formed by the following method. In general, a layer is formed by a vacuum vapor deposition process, an ionization vapor deposition process, a sputtering process, or a plasma process. Alternatively, the layer may be formed by dissolving the compound in an appropriate solvent and subjecting the resultant to a known coating method (e.g., a spin coating method, a dipping method, a casting method, an LB method, or an ink jet method). Here, when the layer is formed by a vacuum vapor deposition method, a solution coating method, or the like, the layer is hard to undergo crystallization and the like and is excellent in stability over time. Further, when the film is formed by a coating method, the film may also be formed in combination with an appropriate binder resin.

Examples of the binder resin include, but not limited to, a poly(vinylcarbazole) resin, a polycarbonate resin, a polyester resin, an ABS resin, an acrylic resin, a polyimide resin, a phenolic resin, an epoxy resin, a silicone resin, and a urea resin. Further, one kind of those binder resins may be used alone as a homopolymer or copolymer, or two or more kinds thereof may be used as a mixture. In addition, a known additive such as a plasticizer, an antioxidant, or an ultraviolet absorber may be used in combination with the binder resin, as necessary.

(Applications of Organic Light-Emitting Device)

The organic light-emitting device according to the present invention may be used as a constituent member for a display apparatus or a lighting apparatus. In addition, the element finds applications in, for example, a light source for exposure of an electrophotographic image forming apparatus or a backlight of a liquid crystal display apparatus.

Here, the display apparatus is an apparatus including the organic light-emitting device of the present invention in a display unit. The display unit includes multiple pixels. The pixels each include the organic light-emitting device of the present invention and a switching element such as a TFT element for controlling the emission luminance of the organic light-emitting device of the present invention. Here, when the TFT element is used as the switching element, the anode or the cathode, which is a constituent member for the organic light-emitting device of the present invention, is electrically connected to a drain electrode or a source electrode of the TFT element. It should be noted that the display apparatus may be used as an image display apparatus such as a PC.

The display apparatus includes an image input unit for inputting information from an area CCD, a linear CCD, a memory card, and the like, and may be an image output apparatus for outputting the input image to a display unit. In addition, a display unit included in an image pickup apparatus or an ink jet printer may be provided with both of an image output function, which displays an image based on image information input from the outside, and an input function, which serves as an operation panel and inputs processing information for an image. Further, the display apparatus may be used for a display unit of a multifunction printer.

Next, a display apparatus using the organic light-emitting device of the present invention is described with reference to the drawing.

FIGURE is a schematic cross-sectional view illustrating an example of a display apparatus including the organic light-emitting device of the present invention and a TFT element as an example of a switching element electrically connected to the organic light-emitting device. Details of the structure are described below.

The display apparatus 20 of FIGURE includes a substrate 1 made of glass or the like and a moisture-proof film 2 for protecting a TFT element or an organic compound layer on the substrate. Further, a gate electrode made of a metal is denoted by reference numeral 3, a gate insulating film 4 is denoted by reference numeral 4, and a semiconductor layer is represented by reference numeral 5.

A TFT element 8 includes the semiconductor layer 5, a drain electrode 6, and a source electrode 7. An insulating film 9 is provided above the TFT element 8. An anode 11 of the organic light-emitting device is connected to the source electrode 7 via a contact hole (through-hole) 10. It should be noted that the display apparatus of the present invention is not limited to the construction of FIGURE, and any one of the anode and a cathode has only to be connected to any one of the source electrode and the drain electrode of the TFT element.

In the display apparatus 20 of FIGURE, an organic compound layer 12 having a single-layer or multi-layer structure is illustrated like a single layer. A first protective layer 14 and a second protective layer 15 for suppressing the degradation of the organic light-emitting device are provided above a cathode 13.

It should be noted that in the display apparatus of the present invention, the switching element constructing the display apparatus is not particularly limited, and a monocrystalline silicon substrate, an MIM element, an a-Si type element, or the like may be used.

EXAMPLES

Hereinafter, the present invention is described in detail by way of examples. In this regard, however, the present invention is by no means limited thereto.

Example 1

Synthesis of Exemplified Compounds D1 and D2

Exemplified Compounds D1 and D2 were synthesized according to a synthesis method to be described below.

(1) Synthesis of Intermediate Compound M1

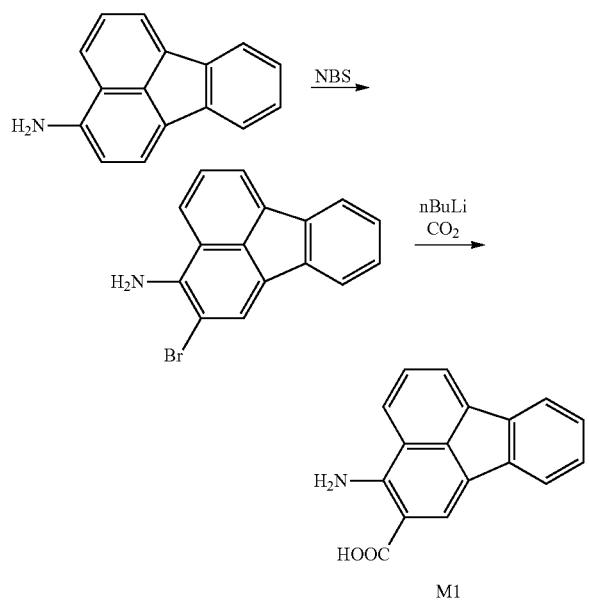

M1

Under an argon atmosphere, the following reagent and solvent were loaded into a 2-L four-necked flask.
3-Aminofluoranthene: 45.4 g (209 mmol)
DMF: 910 mL Next, the reaction solution was cooled to 0° C. with an ice bath in a state where the inside of the reaction system was shielded from light. Next, NBS (37.2 g, 209 mmol) was added to the reaction solution. After that, the ice bath was removed, and then the temperature of the reaction solution was returned to room temperature. Next, the reaction solution was stirred at room temperature for 1 hour. Next, a crystal (yellowish green crystal) precipitated at the time of the injection of the reaction solution into 2 L of ice water was taken by filtration. Next, the crystal taken by filtration was dissolved in 4 L of ethyl acetate, and then the solution was sequentially passed through 50 g of magnesium sulfate and 500 g of Florisil so that the raw material substance was removed. Next, a slurry-like substance produced at the time of the concentration of the filtrate under reduced pressure was filtered. Thus, a crystal was obtained. Next, the resultant crystal was dried under reduced pressure. Thus, 54.0 g of 2-bromofluoranthene-3-amine were obtained (yield: 87.1%).

Subsequently, under an argon atmosphere, the following reagent and solvent were loaded into a 5-L four-necked flask.
2-Bromofluoranthene-3-amine: 55.6 g (188 mmol)
Special grade cyclopentylmethylether: 1.12 L Next, the reaction solution was cooled with an ice bath to an internal temperature of 0° C. while the reaction solution was stirred. Next, 596 mL of a 1.65-M solution of n-BuLi (939 mmol, 5 eq) were dropped to the reaction solution over 30 minutes. Next, the temperature of the reaction solution was returned to room temperature, and then the reaction solution was stirred at the temperature (room temperature) for 3.5 hours. Next, a carbon dioxide gas was blown into the reaction system (the internal temperature of the reaction solution increased from 18° C. to 48° C. as a result of the blowing of the carbon dioxide gas). After that, a gas bag was attached to the reaction system, and then the reaction solution was stirred overnight. Next, a 5-mol/L aqueous solution of hydrochloric acid was dropped into the reaction solution. Here, a crystal precipitated upon dropping of the aqueous solution of hydrochloric acid was filtered, but most of the crystal was a compound except the target product. Under the circumstances, an organic layer obtained by performing a separating operation on the filtrate obtained during the filtration was passed through 500 g of Florisil. Next, the residue obtained by concentrating and exsiccating the filtrate that had been passed was reprecipitated with a THF/CHCl$_3$ mixed solvent. Thus, 10.5 g of a crude crystal were obtained (HPLC purity: 92%). Next, the resultant crude crystal was reprecipitated with a THF/CHCl$_3$ mixed solvent again. Thus, 8.50 g of a crystal A were obtained (HPLC purity: 98%). Next, the filtrate obtained during the second reprecipitation was purified by column chromatography (gel: 1 kg, eluent: heptane/ethyl acetate=1:1). Thus, 900 mg of a crystal B were obtained (HPLC purity: 98%). Next, the crystal A and the crystal B were dissolved in THF while being combined so that a uniform solution was prepared. After that, the solution was concentrated under reduced pressure. Thus, a slurry-like substance was obtained. Next, chloroform was added to the slurry-like substance to take out a crystal C. Next, the crystal C was dried under reduced pressure. Thus, 9.23 g of Intermediate Compound M1 were obtained (yield: 18.6%).

(2) Synthesis of Intermediate Compound M2

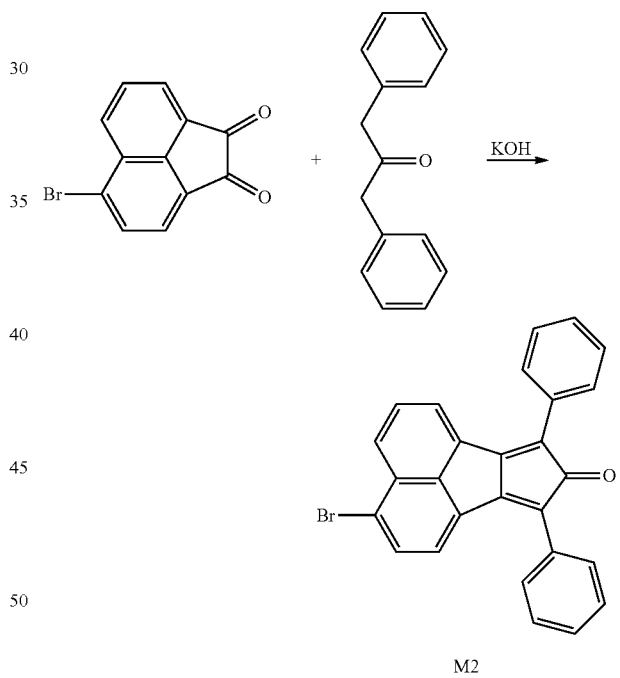

M2

Under a nitrogen atmosphere, the following reagents and solvent were loaded into a 500-mL three-necked reaction vessel.
5-Bromo-acenaphthylene-1,2-dione: 15.0 g (57.5 mmol)
1,3-Diphenylpropan-2-one: 12.1 g (57.5 mmol)
Ethanol: 300 mL Next, 20 mL of a 6-M aqueous solution of sodium hydroxide were dropped into the reaction solution at room temperature. After the completion of the dropping, the reaction solution was heated to 60° C., and then the reaction solution was stirred at the temperature (60° C.) for about 2 hours. Next, a precipitate produced upon cooling of the reaction solution to room temperature was filtered, and then the precipitate was sequentially washed with water and ethanol. Next, the precipitate was dried by heating at 80° C. under reduced pressure. Thus, 22.0 g of Intermediate Compound M2 as a dark green solid were obtained (yield: 88%).

(3) Synthesis of Intermediate Compounds M3 (M3-1 and M3-2)

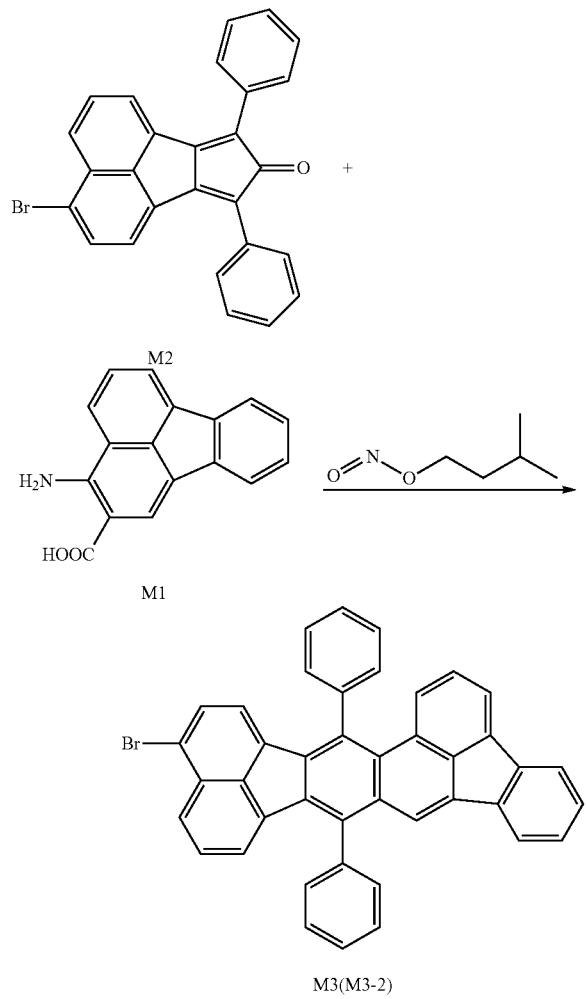

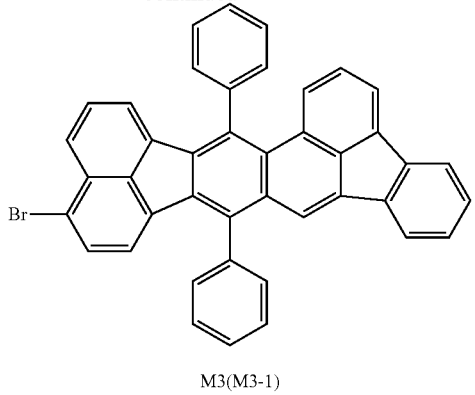

Under a nitrogen atmosphere and room temperature, the following reagents and solvent were loaded into a 1-L three-necked reaction vessel.
Intermediate Compound M2: 18.0 g (41.3 mmol)
Intermediate Compound M1: 14.0 g (53.8 mmol)
Isoamyl nitrite: 8.72 g (74.4 mmol)
Toluene: 720 mL Next, the reaction solution was heated to 95° C., and then the reaction solution was stirred at the temperature (95° C.) for 1.5 hours. Next, the reaction solution was cooled, and then the reaction solution was washed with 1 L of water three times. Next, an organic layer obtained by the washing with water was further washed with a saturated salt solution, and was then dried with magnesium sulfate. Next, a filtrate obtained by filtering the organic layer was concentrated under reduced pressure. Thus, a dark brown liquid was obtained. Next, the resultant dark brown liquid was purified by column chromatography (eluent: toluene/heptane=1/3). Next, a solution obtained during the purification was concentrated under reduced pressure. Thus, a crystal was obtained. Next, 345 mL of methanol were added to the resultant crystal, and then the mixture was subjected to slurry washing by heating. After that, the washed product was left standing to cool to room temperature. A crystal produced at the time of the cooling was filtered. Thus, 21.9 g of a yellow crystal, Intermediate Compounds M3, as a mixture of isomers (M3-1 and M3-2) were obtained (yield: 87%).

(4) Synthesis of Intermediate Compounds M4 (M4-1 and M4-2)

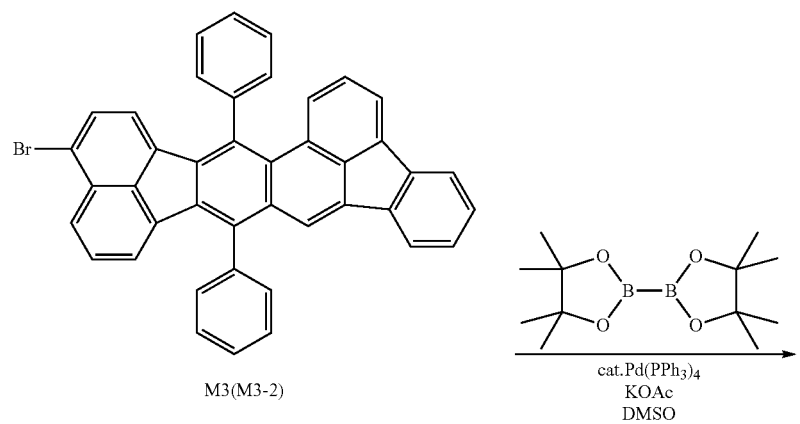

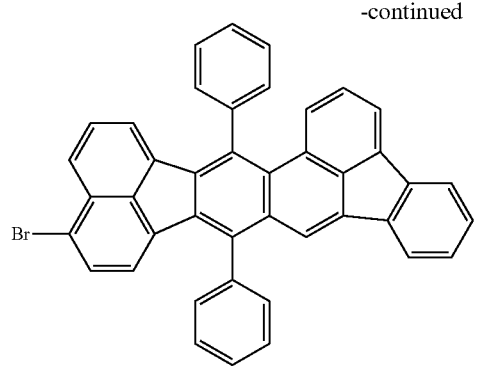

M3(M3-1)

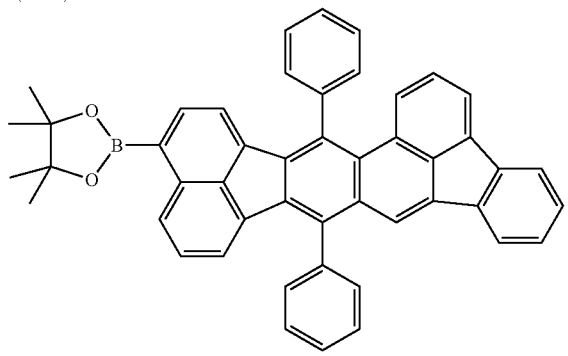

M4(M4-2)

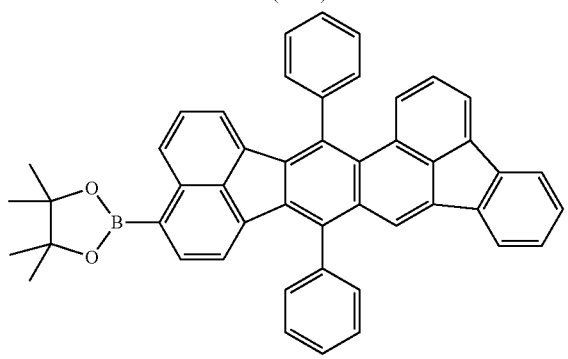

M4(M4-1)

Under a nitrogen atmosphere, the following reagents and solvent were loaded into a 1-L three-necked vessel.
Intermediate compounds M3 (mixture of M3-1 and M3-2): 19.4 g (31.9 mmol)
Bis-dioxabororane: 16.2 g (63.9 mmol)
Potassium acetate: 6.27 g (63.9 mmol)
Tetrakistriphenylphosphine palladium: 1.107 g (0.96 mmol)
DMSO: 388 mL Next, the reaction solution was heated to 100° C., and then the reaction solution was stirred under the temperature (100° C.) for 1.5 hours. Next, the reaction solution was cooled to 30° C., and then 400 mL of methanol were added to the reaction solution. Next, the reaction solution was cooled to 10° C., and then the reaction solution was stirred under the temperature (10° C.) for 1 hour. After that, filtration was performed. Next, 800 mL of methanol were added to the cake obtained by the filtration, and then the mixture was subjected to slurry washing by heating for 1 hour while the solvent (methanol) was refluxed. After that, the washed product was cooled to room temperature and then filtered. Thus, 18.3 g of a crude crystal of Intermediate Compounds M4 were obtained (yield: 87.5%). Next, a solution prepared by dissolving the resultant crude crystal in 265 mL of toluene was purified by column chromatography (eluent: toluene/heptane=1/2→toluene/heptane=1/1). Next, the purified product was subjected to slurry washing by heating with a toluene/methanol mixed solvent. Thus, 9.75 g of a yellow crystal, Intermediate Compounds M4, as a mixture of isomers (M4-1 and M4-2) were obtained (yield: 46.6%).

(5) Synthesis of Intermediate Compound M5

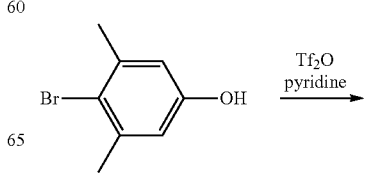

-continued

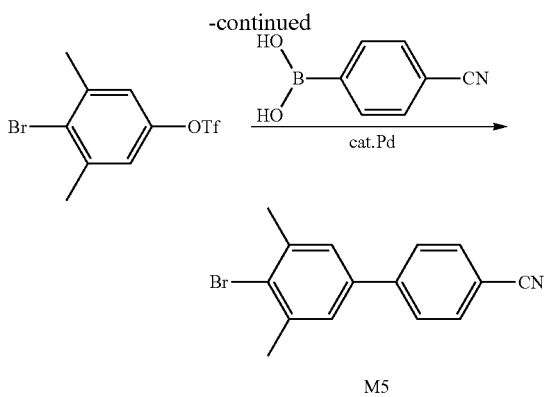

M5

Under a nitrogen atmosphere, the following reagents and solvent were loaded into a 200-mL three-necked vessel.
4-bromo-3,5-dimethylphenol: 3.19 g (16 mmol)
Pyridine: 5.65 g (71 mmol)
Toluene: 65 mL Next, the reaction solution was cooled to 0° C. while being stirred. Next, 13.43 g (48 mmol) of trifluoromethanesulfonic anhydride were slowly dropped to the reaction solution over about 15 minutes while the reaction solution was stirred. After the completion of the dropping, the temperature of the reaction solution was increased to room temperature, and then the reaction solution was stirred under room temperature for an additional one hour. Next, 100 mL of water were added to the reaction solution to terminate the reaction, and 40 mL of toluene were subsequently added to the reaction solution. After that, a separating operation was performed to separate an organic layer. Next, the resultant organic layer was concentrated under reduced pressure, and was then purified by column chromatography (eluent: toluene). A solution obtained at the time of the purification was concentrated under reduced pressure. Thus, 5.94 g of 4-bromo-3,5-dimethylphenyl-trifluoromethanesulfonic acid ester as a colorless, transparent liquid were obtained (yield: 97.1%).

Subsequently, under a nitrogen atmosphere, the following reagents and solvent were loaded into a 500-mL three-necked flask.
4-Bromo-3,5-dimethylphenyl-trifluoromethanesulfonic acid ester: 4.90 g (14.7 mmol)
4-Cyanophenylboronic acid: 2.05 g (14.0 mmol)
Dioxane: 245 mL
Potassium carbonate: 4.07 g (29.4 mmol)
Tetrakistriphenylphosphine palladium: 0.17 g (0.15 mmol)

Next, the reaction solution was heated to 80° C., and then the reaction solution was stirred under the temperature (80° C.) for 1.5 hours. Next, the reaction solution was left standing to cool to room temperature. After that, 100 mL of toluene and 100 mL of water were added to the reaction solution to perform a separating operation so that an organic layer was separated. Next, the resultant organic layer was dried with magnesium sulfate. After that, a filtrate obtained by filtering the organic layer was concentrated under reduced pressure. Thus, 4.64 g of a crude crystal of Intermediate Compound M5 were obtained. Next, a solution prepared by mixing the resultant crude crystal and toluene was purified by column chromatography (eluent: toluene/heptane=1/5→toluene/heptane=1/4). After that, the purified product was concentrated and exsiccated. Thus, 1.54 g of Intermediate Compound M5 as a white crystal were obtained (yield: 37%).

(6) Synthesis of Exemplified Compounds D1 and D2

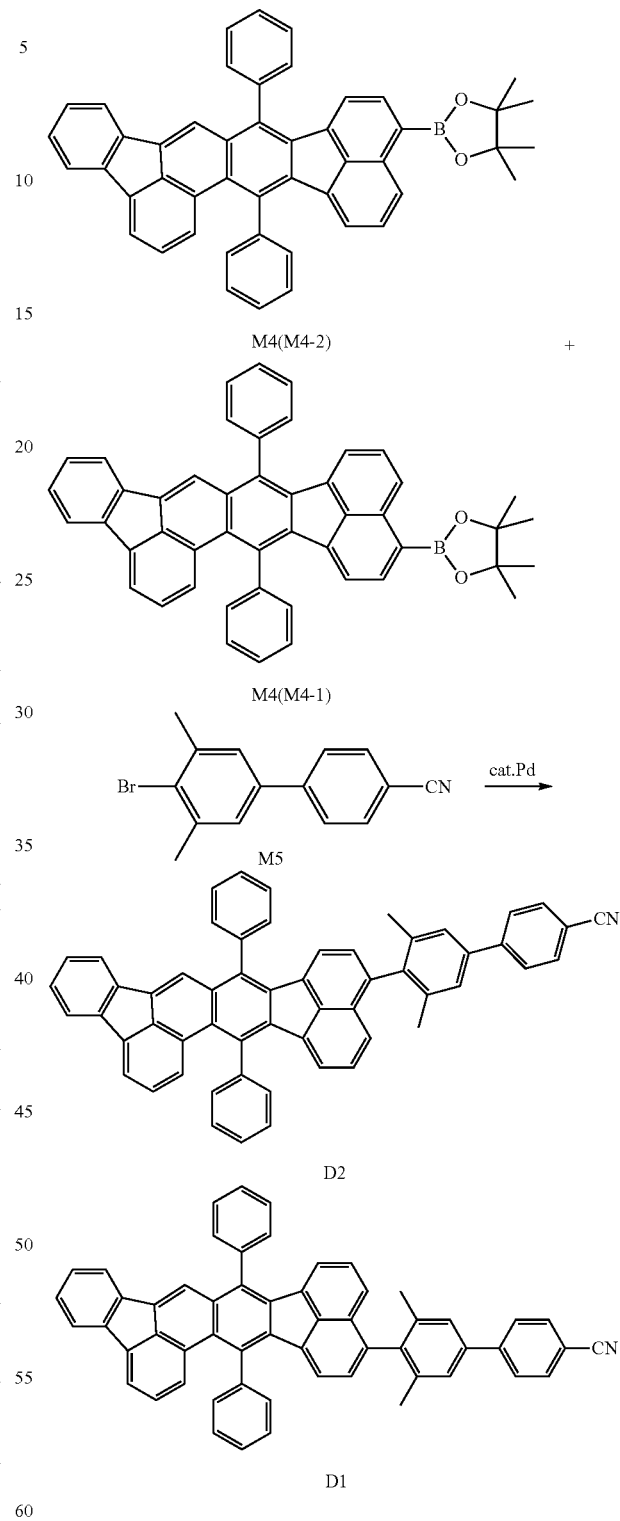

Under a nitrogen atmosphere, the following reagents and solvents were loaded into a 500-mL three-necked flask.
Intermediate Compounds M4 (the mixture of M4-1 and M4-2): 4.40 g (6.72 mmol)
Intermediate Compound M5: 1.54 g (5.38 mmol)
Toluene: 220 mL
Ethanol: 110 mL Sodium carbonate: 1.42 g (13.4 mmol)

Water: 100 mL

Tetrakistriphenylphosphine palladium: 0.39 g (0.34 mmol)

Next, the reaction solution was heated to 70° C., and then the reaction solution was stirred under the temperature (70° C.) for 3 hours. Next, the reaction solution was left standing to cool to room temperature. After that, the reaction solution was washed with 100 mL of water twice. Thus, an organic layer was obtained. Next, the organic layer was dried with magnesium sulfate. After that, a filtrate obtained by filtering the solution was concentrated under reduced pressure. Thus, a yellow crude crystal was obtained. Next, the crude crystal was dissolved in a solvent prepared by mixing 60 ml of toluene and 60 mL of heptane, and then the solution was purified by column chromatography (eluent: toluene/heptane=1/1→toluene/heptane=2/1). Next, the solution was concentrated under reduced pressure. After that, methanol was added to the concentrated product, and then the mixture was subjected to slurry washing by heating. Thus, 3.26 g of a mixture of Exemplified Compounds D1 and D2 as a yellow crystal were obtained (yield: 66%). It should be noted that Exemplified Compound D1 is synthesized from Intermediate Compound M4-1 and Exemplified Compound D2 is synthesized from Intermediate Compound M4-2.

Mass spectrometry confirmed 733 as the M⁺ of the compound. In addition, NMR measurement confirmed that the mixing ratio between Exemplified Compounds D1 and D2 was 1:1.

$^1$H-NMR (CDCl$_3$): δ (ppm)=8.20 (s, 2H), 7.89-7.97 (m, 4H), 7.83-7.65 (m, 30H), 7.40-7.37 (m, 6H), 7.34-7.28 (m, 6H), 7.25-7.20 (m, 4H), 7.12 (d, 1H, J=7.99 Hz), 7.09 (d, 1H, J=7.99 Hz), 6.61 (d, 1H, J=7.99 Hz), 6.53 (dt, 1H, J1=7.99 Hz, J2=3.99 Hz), 6.38 (d, 1H, J=7.99 Hz), 6.30 (dd, 1H, J1=7.99 Hz, J2=3.99 Hz), 1.97 (s, 12H)

Further, the emission spectrum of the mixture of Exemplified Compounds D1 and D2 in a toluene solution having a concentration of $1.0 \times 10^{-6}$ mol/L was measured. Specifically, photoluminescence measurement was performed with an F-5400 manufactured by Hitachi, Ltd. at an excitation wavelength of 418 nm. As a result, a blue light emission spectrum having the maximum intensity in an emission peak at 450 nm was observed.

Example 2

Synthesis of Exemplified Compounds D87 and D88

Synthesis was performed by the same method as that in Example 1 except that Intermediate Compound M6 shown below was used instead of Intermediate Compound M5 in Example 1(6). Thus, (a mixture of) Exemplified Compounds D87 and D88 was obtained. Hereinafter, specific methods of synthesizing Intermediate Compound M6, and Exemplified Compounds D87 and D88 are described.

(1) Synthesis of Intermediate Compound M6

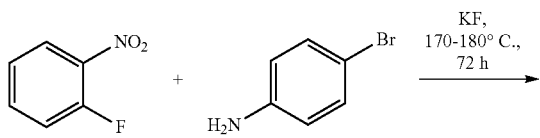

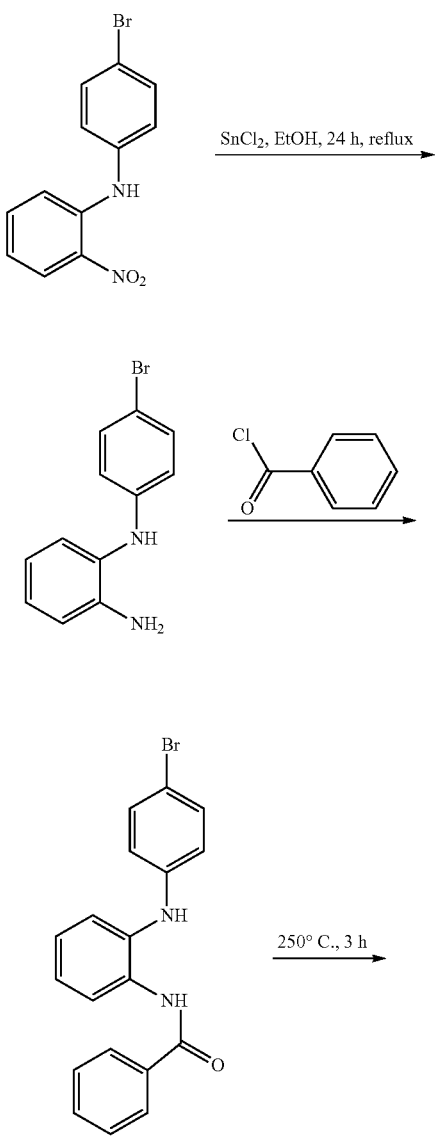

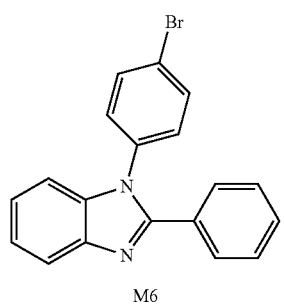

30 Grams of Intermediate Compound M6 were synthesized by using 1-fluoro-2-nitrobenzene and 1-bromo-4-aminobenzene as starting materials according to the method described in Chemistry of Materials, 2009, 21 (12), 2452.

(2) Synthesis of Exemplified Compounds D87 and D88

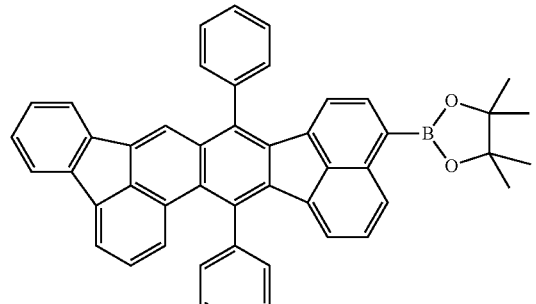

M4(M4-2)

+

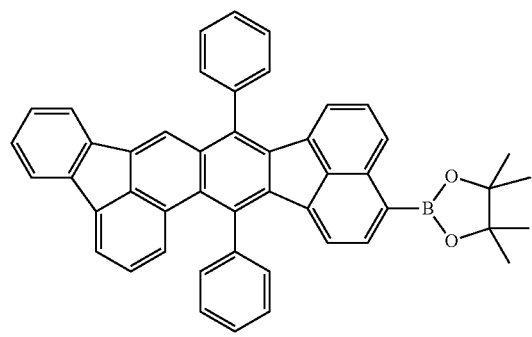

M4(M4-1)

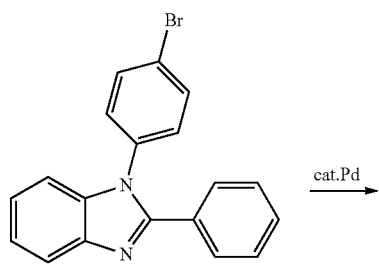

M6

$\xrightarrow{\text{cat.Pd}}$

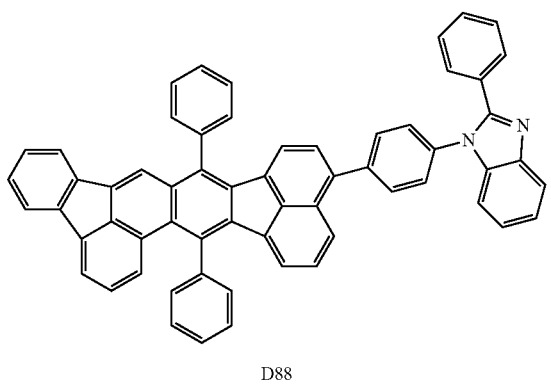

D88

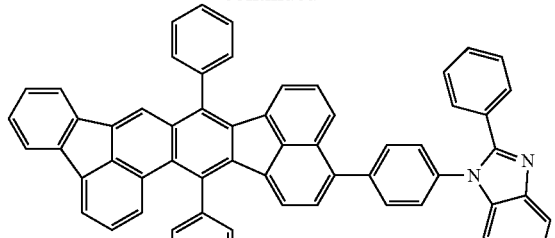

D87

Under a nitrogen atmosphere, the following reagents and solvents were loaded into a 200-mL three-necked flask.
Intermediate Compounds M4 (the mixture of M4-1 and M4-2): 1.30 g (1.99 mmol)
Intermediate Compound M6: 1.54 g (1.39 mmol)
Toluene: 39 mL
Ethanol: 13 mL
Sodium carbonate: 0.42 g (3.97 mmol)
Water: 13 mL
Tetrakistriphenylphosphine palladium: 0.12 g (0.11 mmol)

Next, the reaction solution was heated to 70° C., and then the reaction solution was stirred under the temperature (70° C.) for 5 hours. Next, the reaction solution was left standing to cool to room temperature. After that, the reaction solution was washed with 100 mL of water three times. Thus, an organic layer was obtained. Next, the organic layer was dried with magnesium sulfate. After that, a filtrate obtained by filtering the solution was concentrated under reduced pressure. Thus, a yellow crude crystal was obtained. Next, a solution obtained by mixing the resultant crude crystal and 19 mL of toluene was purified by column chromatography (eluent: toluene/ethyl acetate=9/1→toluene/ethyl acetate=5/1). Next, the solution was concentrated. After that, methanol was added to the concentrated product, and then the mixture was subjected to slurry washing by heating. Thus, 0.96 g of a mixture of Exemplified Compounds D87 and D88 as a yellow crystal were obtained (yield: 58%). It should be noted that Exemplified Compound D87 is synthesized from Intermediate Compound M4-1 and Exemplified Compound D88 is synthesized from Intermediate Compound M4-2.

Mass spectrometry confirmed 796 as the M+ of the compound. In addition, NMR measurement confirmed that the mixing ratio between Exemplified Compounds D87 and D88 was 1:1.

$^1$H-NMR (CDCl$_3$): δ (ppm)=8.21 (s, 1H), 8.20 (s, 1H), 7.93-7.63 (m, 38H), 7.43-7.29 (m, 28H), 6.59 (dd, 2H, J1=7.99 Hz, J2=3.99 Hz), 6.35 (d, 2H, J=7.99 Hz)

Further, the emission spectrum of the mixture of Exemplified Compounds D87 and D88 in a toluene solution having a concentration of $1.0 \times 10^{-6}$ mol/L was measured. Specifically, photoluminescence measurement was performed with an F-5400 manufactured by Hitachi, Ltd. at an excitation wavelength of 418 nm. As a result, a blue light emission spectrum having the maximum intensity in an emission peak at 455 nm was observed.

Example 3

Synthesis of Exemplified Compounds D83 and D84

Synthesis was performed by the same method as that in Example 1 except that Intermediate Compound M7 shown below was used instead of Intermediate Compound M5 in Example 1(6). Thus, (a mixture of) Exemplified Compounds D83 and D84 was obtained. Hereinafter, specific methods of synthesizing Intermediate Compound M7, and Exemplified Compounds D83 and D84 are described.

(1) Synthesis of Intermediate Compound M7

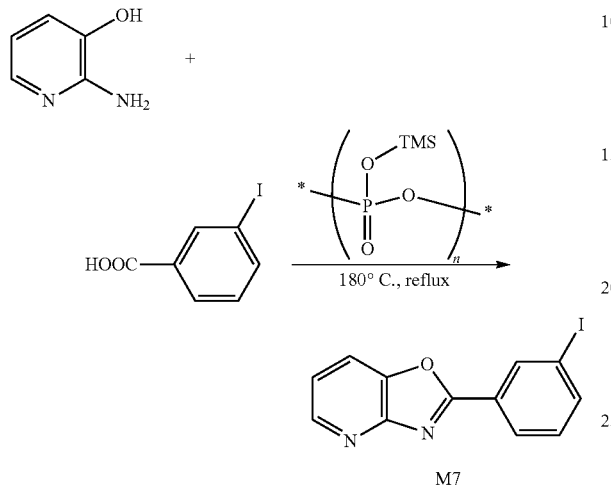

22 Grams of Intermediate Compound M7 were synthesized by using 3-hydroxy-2-aminopyridine and 3-iodo-1-carboxylbenzene as starting materials according to the method described in Heterocycles, 2001, 55, 1329.

(2) Synthesis of Exemplified Compounds D83 and D84

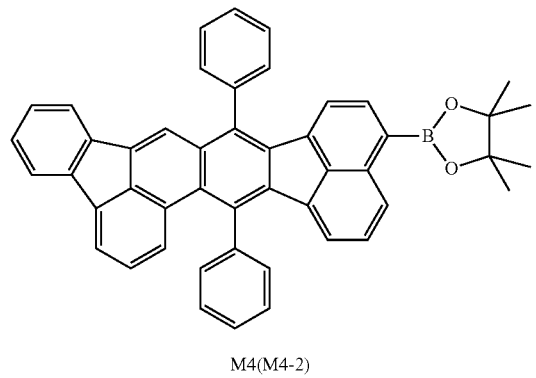

M4(M4-2)

+

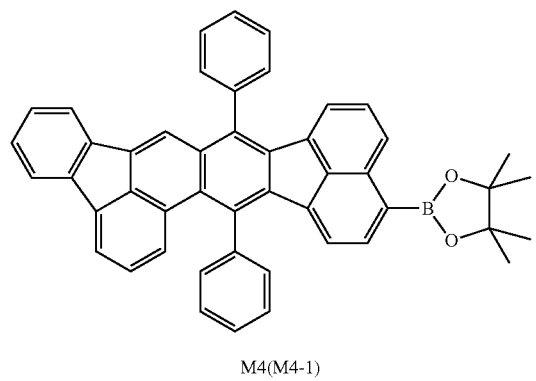

M4(M4-1)

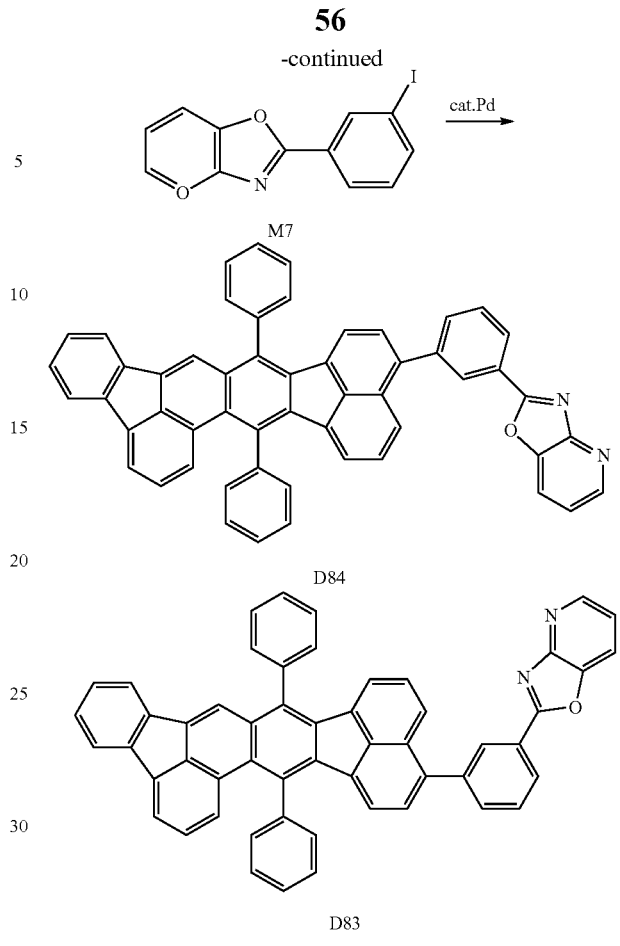

Under a nitrogen atmosphere, the following reagents and solvents were loaded into a 200-mL three-necked flask.
Intermediate Compounds M4 (the mixture of M4-1 and M4-2): 1.40 g (2.10 mmol)
Intermediate Compound M7 0.48 g (1.39 mmol)
Toluene: 70 mL
Ethanol: 30 mL
Sodium carbonate: 0.17 g (3.97 mmol)
Water: 30 mL
Tetrakistriphenylphosphine palladium: 0.12 g (0.11 mmol)

Next, the reaction solution was heated to 70° C., and then the reaction solution was stirred under the temperature (70° C.) for 2.5 hours. Next, the reaction solution was left standing to cool to room temperature. After that, the reaction solution was washed with 100 mL of water three times. Thus, an organic layer was obtained. Next, the organic layer was dried with magnesium sulfate. After that, a filtrate obtained by filtering the solution was concentrated under reduced pressure. Thus, a yellow crude crystal was obtained. Next, a solution obtained by mixing the resultant crude crystal and 20 mL of toluene was purified by column chromatography (eluent: toluene/ethyl acetate=9/1). Next, the solution was concentrated. After that, methanol was added to the concentrated product, and then the mixture was subjected to slurry washing by heating. Thus, 0.93 g of a mixture of Exemplified Compounds D83 and D84 as a yellow crystal were obtained (yield: 56%). It should be noted that Exemplified Compound D83 is synthesized from Intermediate Compound M4-1 and Exemplified Compound D84 is synthesized from Intermediate Compound M4-2.

Mass spectrometry confirmed 722 as the $M^+$ of the compound.

In addition, NMR measurement confirmed that the mixing ratio between Exemplified Compounds D83 and D84 was 1:1.

$^1$H-NMR (CDCl$_3$): δ (ppm)=8.59 (dd, 2H, J1=3.99 Hz, J2=1.33 Hz), 8.48 (s, 2H), 8.38 (d, 2H, J=7.99 Hz), 8.22 (s, 1H), 8.21 (s, 1H), 7.88-7.64 (m, 34H), 7.42-7.28 (m, 14H), 6.59 (dd, 2H, J1=9.99 Hz, J2=7.99 Hz), 6.35 (dd, 2H, J1=7.99 Hz, J2=7.99 Hz)

Further, the emission spectrum of the mixture of Exemplified Compounds D83 and D84 in a toluene solution having a concentration of 1.0×10$^{-6}$ mol/L was measured. Specifically, photoluminescence measurement was performed with an F-5400 manufactured by Hitachi, Ltd. at an excitation wavelength of 418 nm. As a result, a blue light emission spectrum having the maximum intensity in an emission peak at 453 nm was observed.

Comparative Example 1

Synthesis of Comparative Compounds R1 and R2

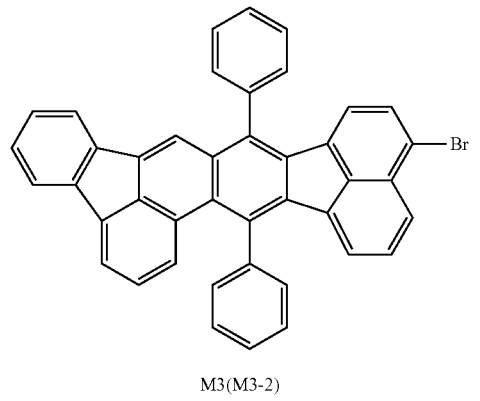

M3(M3-2)

+

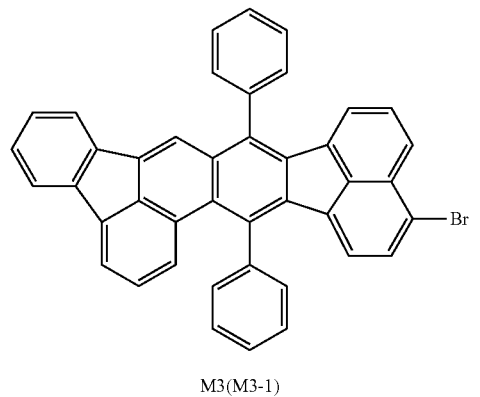

M3(M3-1)

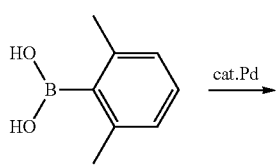

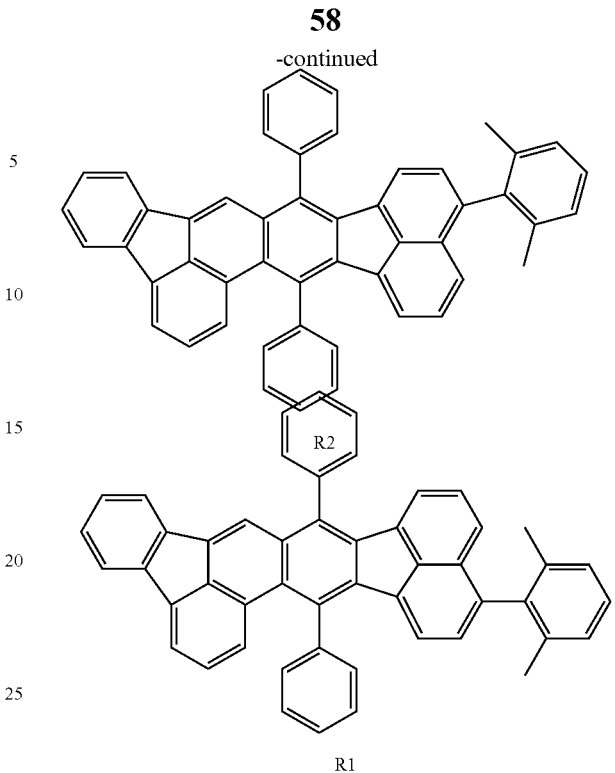

R1

Synthesis was performed by the same method as that in Example 1 except that in Example 1(6), Intermediate Compounds M3 (the mixture of M3-1 and M3-2) were used instead of Intermediate Compounds M4 (the mixture of M4-1 and M4-2), and 2,6-dimethylphenylboronic acid was used instead of Intermediate Compound M5. Thus, 0.95 g of Comparative Compounds R1 and R2 as a mixture of R1 and R2 was obtained (yield: 75%).

Mass spectrometry confirmed 632 as the M$^+$ of the compound.

Further, the emission spectrum of the mixture of Comparative Compounds R1 and R2 in a toluene solution having a concentration of 1.0×10$^{-6}$ mol/L was measured. Specifically, photoluminescence measurement was performed with an F-5400 manufactured by Hitachi, Ltd. at an excitation wavelength of 414 nm. As a result, a blue light emission spectrum having the maximum intensity in an emission peak at 447 nm was observed.

Comparative Example 2

Synthesis of Comparative Compounds R3 and R4

M3(M3-2)

+

-continued

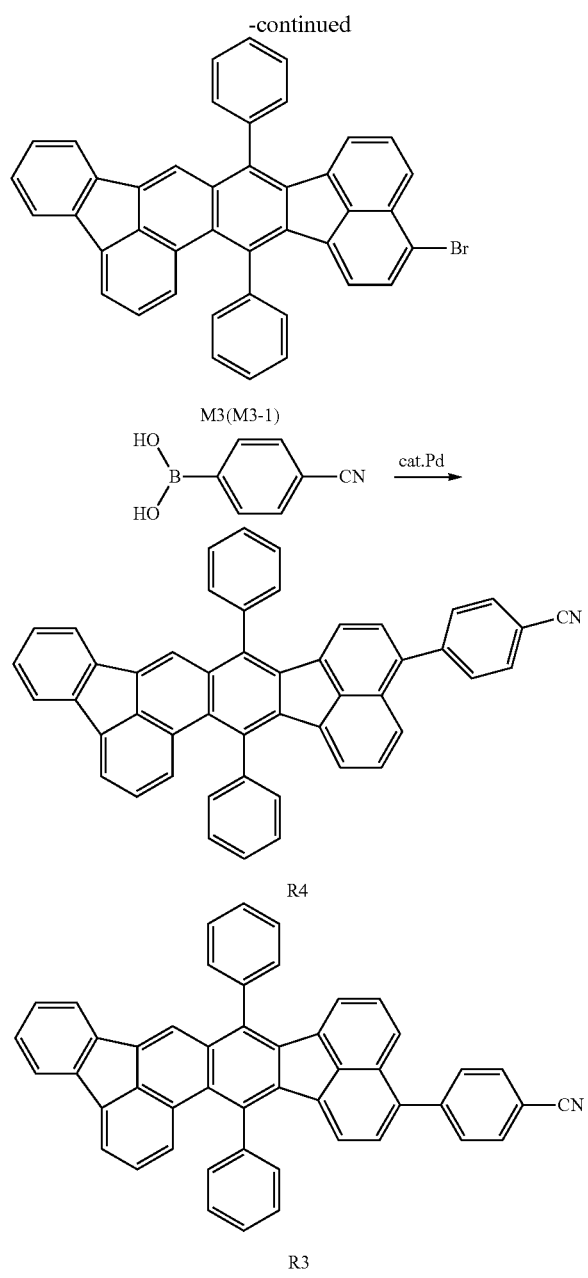

Synthesis was performed by the same method as that in Example 1 except that in Example 1(6), Intermediate Compounds M3 (the mixture of M3-1 and M3-2) were used instead of Intermediate Compounds M4 (the mixture of M4-1 and M4-2), and 4-cyanophenylboronic acid was used instead of Intermediate Compound M5. Thus, 0.8 g of Comparative Compounds R3 and R4 as a mixture of R3 and R4 was obtained (yield: 70%).

Mass spectrometry confirmed 629 as the M+ of the compound.

Further, the emission spectrum of the mixture of Comparative Compounds R3 and R4 in a toluene solution having a concentration of $1.0 \times 10^{-6}$ mol/L was measured. Specifically, photoluminescence measurement was performed with an F-5400 manufactured by Hitachi, Ltd. at an excitation wavelength of 414 nm. As a result, a blue light emission spectrum having the maximum intensity in an emission peak at 458 nm was observed.

(Comparison of Fluorescent Quantum Yields and Oxidation-Reduction Potentials)

The respective compounds obtained in Examples 1 to 3 (Exemplified Compounds D1, D2, D83, D84, D87, and D88), and the compounds obtained in Comparative Examples 1 and 2 (Comparative Compounds R1, R2, R3, and R4) were evaluated for their quantum yields and oxidation-reduction potentials by methods to be described below.

(1) Fluorescent Quantum Yield

First, a toluene solution having a concentration of $10^{-6}$ mol/l was prepared. Next, a value for the quantum yield of the prepared solution when an excitation wavelength was set to 414 nm was measured with an absolute PL quantum yield measurement system (manufactured by Hamamatsu Photonics K.K., trade name: C9920). Then, a relative value for its emission quantum yield when the emission quantum yield of the mixture of Comparative Compounds R1 and R2 (mixing ratio=1:1) was set to 1 was determined. Table 1 shows the results.

(2) Oxidation-Reduction Potential

An oxidation-reduction potential was measured by a cyclic voltammetry method as described below. Specifically, an oxidation potential and a reduction potential were measured with 0.1 mol/L of tetrabutylammonium perchlorate as a supporting electrolytic substance under the following conditions. The oxidation potential was measured in a methylene chloride solution of each compound having a concentration of $1 \times 10^{-6}$ mol/L or more and $1 \times 10^{-4}$ mol/L or less. The reduction potential was measured in an N,N-dimethylformamide solution of each compound having a concentration of $1 \times 10^{-6}$ mol/L or more and $1 \times 10^{-4}$ mol/L or less. It should be noted that a measurement temperature during each measurement was set to 25° C., and the measurement was performed by using $Ag/AgNO_3$ as a reference electrode, a platinum electrode as a counter electrode, and glassy carbon as a working electrode. Table 1 shows the results.

TABLE 1

| | | Fluorescent quantum yield (Note 1) | $E_{ox}$ [V] (Note 2) | $E_{red}$ [V] (Note 2) |
|---|---|---|---|---|
| Example 1 | D1, D2 | 1.16 | 1.18 | −1.89 |
| Example 2 | D87, D88 | 1.12 | 1.19 | −1.86 |
| Example 3 | D83, D84 | 1.10 | 1.20 | −1.86 |
| Comparative Example 1 | R1, R2 | 1.00 | 1.15 | −1.89 |
| Comparative Example 2 | R3, R4 | 0.90 | 1.19 | −1.81 |

(Note 1) A relative value with reference to R1 and R2 (1.00)
(Note 2) A reference electrode: $Ag/AgNO_3$ ($Ag/Ag^+$ system)

As can be seen from Table 1, the fluorescent quantum yield of the acenaphtho[1,2-k]benzo[e]acephenanthrene derivative of the present invention increased as compared with that of Comparative Compounds R1 and R2 by a factor of 1.1 or more.

In addition, Comparative Compounds R3 and R4 each obtained by directly introducing a 4-cyanophenyl group, which is electron-withdrawing, into the 12-position or 13-position of an acenaphtho[1,2-k]benzo[e]acephenanthrene skeleton have the deepest reduction potential, and hence an effect of the introduction of the 4-cyanophenyl group is large. On the other hand, however, their fluorescent quantum yield was found to reduce as compared with that of Comparative Compounds R1 and R2.

The foregoing showed that the acenaphtho[1,2-k]benzo[e]acephenanthrene derivative of the present invention was a material having a deep reduction potential, and at the same time, having a high fluorescent quantum yield as a result of the introduction of a specific electron-withdrawing substituent into a specific position of its acenaphtho[1,2-k]benzo[e]acephenanthrene skeleton via a phenyl group.

Example 4

Produced in this example was an organic light-emitting device in which an anode, a hole transport layer, an emission layer, a hole/exciton blocking layer, an electron transport layer, and a cathode were sequentially formed on a substrate. Hereinafter, part of the materials used in this example are shown.

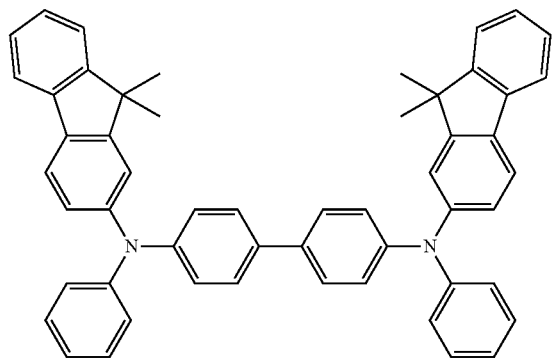

G1

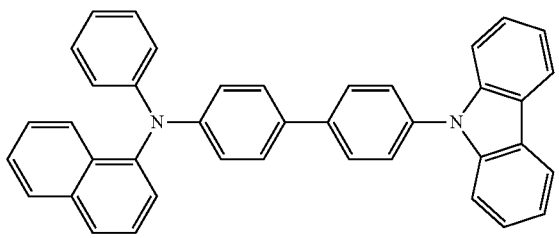

G2

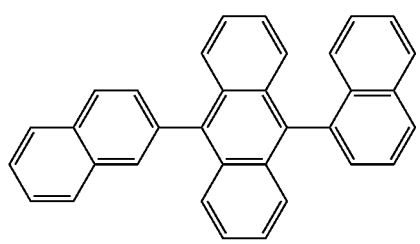

G3

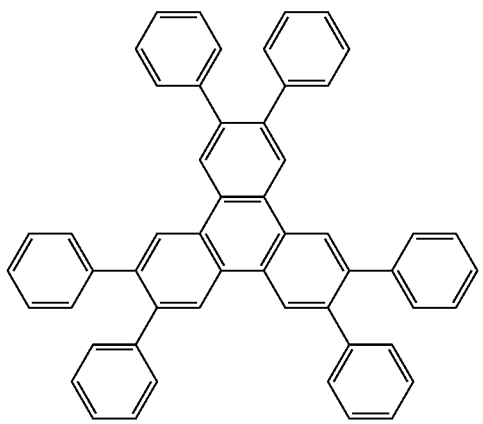

G4

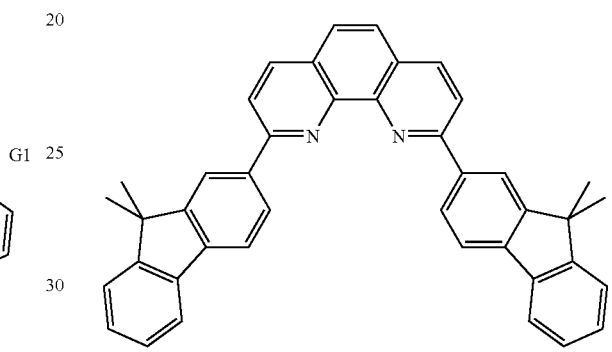

G5

A specific method of producing the organic light-emitting device is described below.

ITO was formed into a film by a sputtering method on a glass substrate. Thus, the anode was formed. In this case, the thickness of the anode was set to 120 nm. The substrate on which the ITO electrode had been formed as described above was used as a transparent conductive supporting substrate (ITO substrate) in the following steps. Next, organic compound layers and electrode layers described in Table 2 below were continuously formed on the ITO substrate by vacuum vapor deposition through resistance heating in a vacuum chamber at $1\times10^{-5}$ Pa. In this case, an opposite electrode (a metal electrode layer or the cathode) was produced so as to have an area of 3 mm$^2$.

TABLE 2

| | Material | Thickness [nm] |
|---|---|---|
| Hole injection layer | G1 | 20 |
| Hole transport layer | G2 | 10 |
| Emission layer | Host: G3<br>Guest (Note 3):<br>D1, D2 (Note 4) | 30 |
| Hole/exciton blocking layer | G4 | 10 |
| Electron transport layer | G5 | 30 |
| First metal electrode layer | LiF | 1 |
| Second metal electrode layer | Al | 100 |

(Note 3) A weight ratio of the guest to the host: 2%
(Note 4) The mixing ratio (weight ratio) between D1 and D2 is 1:1.

The element characteristics of the resultant element were measured and evaluated. Specifically, its current-voltage characteristics were measured with a microammeter 4140B manufactured by Hewlett-Packard Company, and its emission luminance was measured with a BM7 manufactured by TOPCON CORPORATION. Table 3 shows the results of the measurement.

Examples 5 and 6

Organic light-emitting devices were each produced by the same method as that in Example 4 except that the guest in Example 4 was appropriately changed to a compound described in Table 3. The element characteristics of the resultant elements were measured and evaluated in the same manner as in Example 4. Table 3 shows the results of the measurement.

Comparative Example 3

An organic light-emitting device was produced by the same method as that in Example 4 except that the guest in Example 4 was appropriately changed to Comparative Compounds R1 and R2 (the weight mixing ratio between R1 and R2 was 1:1). The element characteristics of the resultant element were measured and evaluated in the same manner as in Example 4. Table 3 shows the results of the measurement.

TABLE 3

| | Guest | External quantum efficiency [%] @10 mA/cm² | CIE chromaticity coordinates (X, Y) | Half lifetime [h] @100 mA/cm² |
|---|---|---|---|---|
| Example 4 | D1, D2 | 9.1 | (0.14, 0.20) | 320 |
| Example 5 | D83, D84 | 8.1 | (0.15, 0.26) | 350 |
| Example 6 | D87, D88 | 8.6 | (0.15, 0.27) | 400 |
| Comparative Example 3 | R1, R2 | 8.5 | (0.15, 0.20) | 230 |

(Results and Discussion)

The fused polycyclic compound of the present invention is an organic compound showing a high quantum yield and blue light emission, and when the compound is used as a component for an organic light-emitting device, a light-emitting device having good chromaticity and high efficiency, and at the same time, having particularly good durability can be provided.

REFERENCE SIGNS LIST

8: TFT element
11: anode
12: organic compound layer
13: cathode

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-120164, filed May 30, 2011, which is hereby incorporated by reference herein in its entirety.

What is claimed is:

1. A fused polycyclic compound, comprising a compound represented by at least one of the following general formulae (1), (2), (8) and (9):

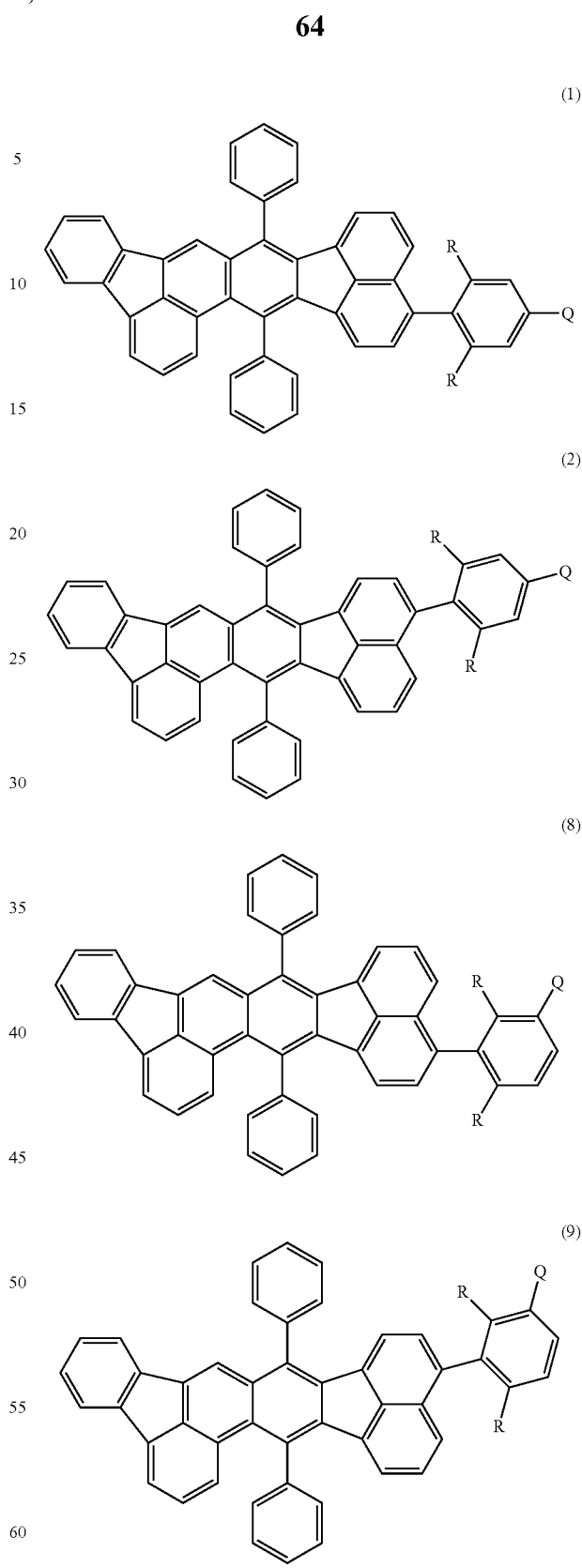

in the formulae (1), (2), (8) and (9), R represents one of a hydrogen atom and a methyl group, and Q represents an electron-withdrawing substituent selected from the group consisting of the following general formulae (3) to (7):

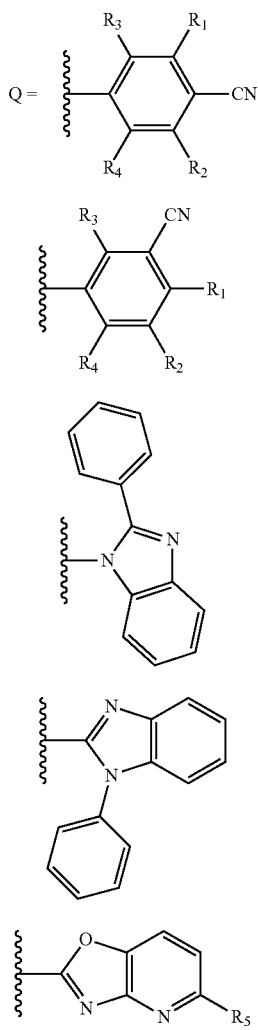

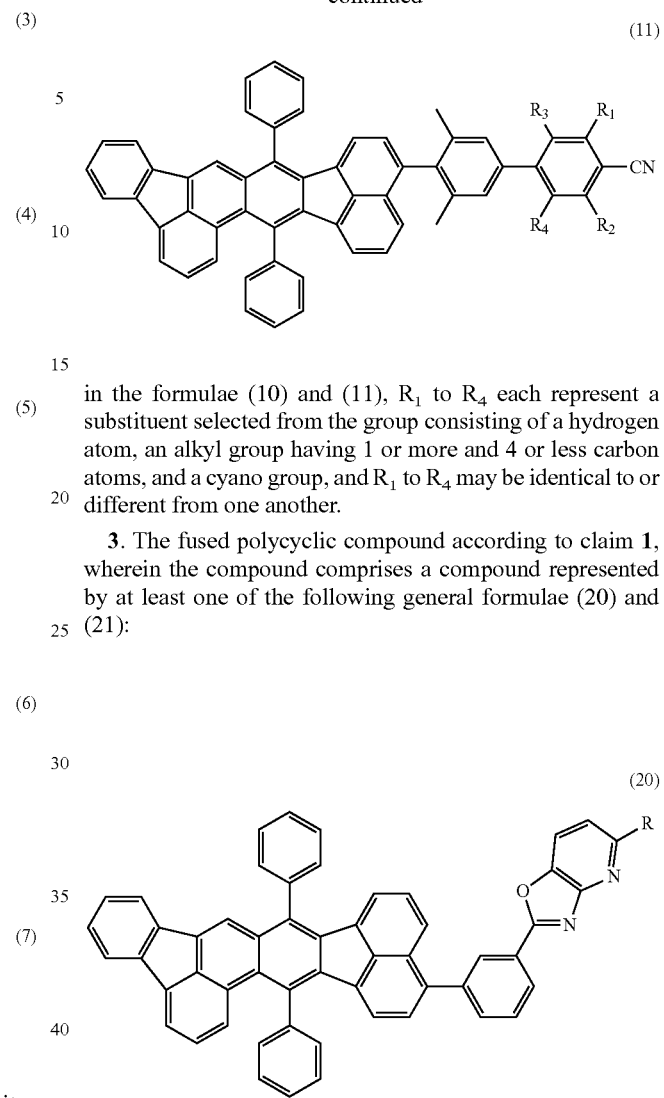

in the formulae (3) and (4), R₁ to R₄ each represent a substituent selected from the group consisting of a hydrogen atom, an alkyl group having 1 or more and 4 or less carbon atoms, and a cyano group, and R₁ to R₄ may be identical to or different from one another, and in the formula (7), R₅ represents one of a hydrogen atom and a methyl group.

2. The fused polycyclic compound according to claim 1, wherein the compound comprises a compound represented by at least one of the following general formulae (10) and (11):

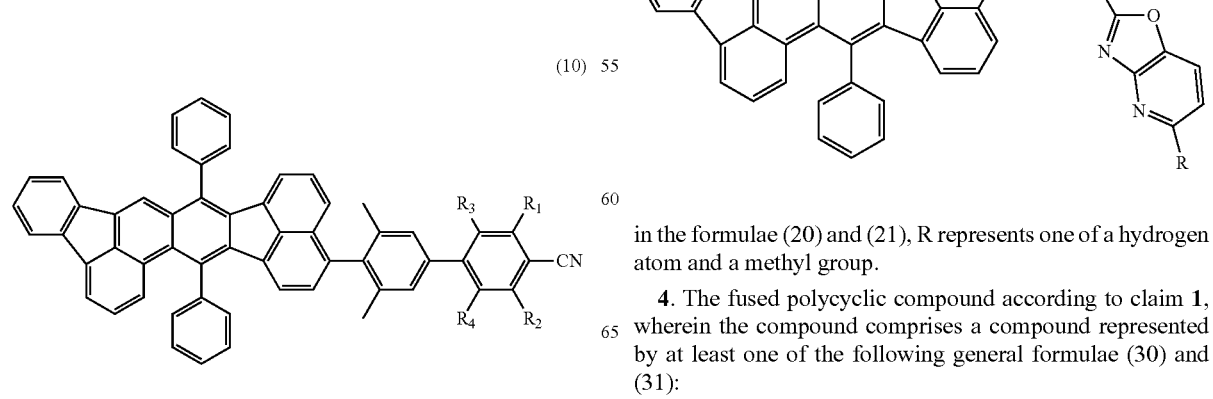

in the formulae (10) and (11), R₁ to R₄ each represent a substituent selected from the group consisting of a hydrogen atom, an alkyl group having 1 or more and 4 or less carbon atoms, and a cyano group, and R₁ to R₄ may be identical to or different from one another.

3. The fused polycyclic compound according to claim 1, wherein the compound comprises a compound represented by at least one of the following general formulae (20) and (21):

in the formulae (20) and (21), R represents one of a hydrogen atom and a methyl group.

4. The fused polycyclic compound according to claim 1, wherein the compound comprises a compound represented by at least one of the following general formulae (30) and (31):

(30)

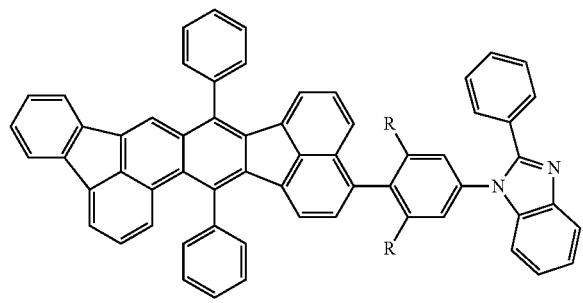

(31)

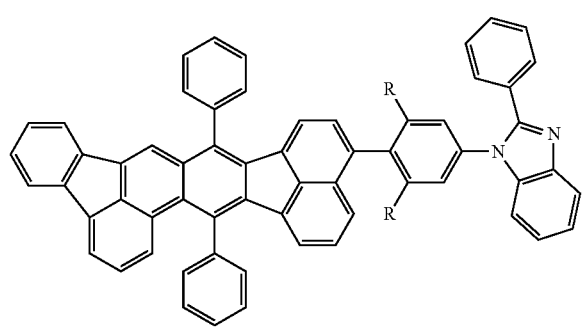

in the formulae (30) and (31), R represents one of a hydrogen atom and a methyl group.

5. An organic light-emitting device, comprising:
an anode;
a cathode; and
an organic compound layer disposed between the anode and the cathode,
wherein at least one layer of the organic compound layer has the fused polycyclic compound according to claim 1.

6. The organic light-emitting device according to claim 5, wherein the fused polycyclic compound is incorporated into an emission layer.

7. The organic light-emitting device according to claim 6, wherein the emission layer comprises a host and a guest.

8. A display apparatus, comprising multiple pixels, wherein the pixels each have the organic light-emitting device according to claim 5 and a switching element connected to the organic light-emitting device.

9. An image display apparatus, comprising:
an input portion for inputting an image; and
a display portion for displaying the image,
wherein:
the display portion has multiple pixels; and
the pixels each have the organic light-emitting device according to claim 5 and a switching element connected to the organic light-emitting device.

* * * * *